United States Patent
Aureli et al.

(10) Patent No.: US 10,568,344 B2
(45) Date of Patent: Feb. 25, 2020

(54) METHODS OF IMPROVING ANIMAL PERFORMANCE

(71) Applicants: Novozymes A/S, Bagsvaerd (DK); DSM IP Assets B.V., Heerlen (NL)

(72) Inventors: Raffaella Aureli, Kaiseraugst (CH); Estefania Perez Calvo, Kaiseraugst (CH); Rual Lopez Ulibarri, Kaiseraugst (CH); Dorthe Hoej Sandvang, Slangerup (DK); Juliane Charlotte Gregaard Thoegersen, Vedbaek (DK); Peter Bjarke Olsen, Copenhagen (DK); Preben Nielsen, Horsholm (DK); Marianne Thorup Cohn, Copenhagen (DK)

(73) Assignees: Novozymes A/S, Bagsvaerd (DK); DSM IP Assets B.V., Heerlen (NL)

( * ) Notice: Subject to any disclaimer, the term of this patent is extended or adjusted under 35 U.S.C. 154(b) by 10 days.

(21) Appl. No.: 15/737,763

(22) PCT Filed: Jul. 4, 2016

(86) PCT No.: PCT/EP2016/065701
§ 371 (c)(1),
(2) Date: Dec. 19, 2017

(87) PCT Pub. No.: WO2017/001703
PCT Pub. Date: Jan. 5, 2017

(65) Prior Publication Data
US 2018/0184688 A1    Jul. 5, 2018

(30) Foreign Application Priority Data
Jul. 2, 2015 (EP) .................... 15174930

(51) Int. Cl.
*A61K 38/47* (2006.01)
*A23K 50/30* (2016.01)
*A23K 50/75* (2016.01)
*A23K 20/189* (2016.01)

(52) U.S. Cl.
CPC ........... *A23K 20/189* (2016.05); *A23K 50/30* (2016.05); *A23K 50/75* (2016.05); *A61K 38/47* (2013.01); *C12Y 302/01017* (2013.01)

(58) Field of Classification Search
CPC .... A23K 20/189; A23K 50/75; A23K 20/174; A23K 20/184; A23K 20/20; A23K 40/20; A23K 40/25; A23K 50/80; A23K 20/147; A23K 40/30; A23K 50/30; C12N 9/2462; C12N 15/1003; C12N 15/62; C12N 9/16; C12N 9/24; C12N 9/54; C12Y 302/01017; C12Y 301/03026; C12Y 304/21062
See application file for complete search history.

(56) References Cited

FOREIGN PATENT DOCUMENTS

| GB | 2379166 A | 3/2003 |
|---|---|---|
| WO | 00/21381 A1 | 4/2000 |
| WO | 2004/026334 A1 | 4/2004 |
| WO | 2006/034710 A1 | 4/2006 |
| WO | 2013/076253 A1 | 5/2013 |

OTHER PUBLICATIONS

Houghten et al. (Vaccines, 1986, Edited by Fred Brown: Cold Spring Harbor Laboratory) pp. 21-25 (Year: 1986).*
Masschalck et al., Journal of Food Protection, vol. 65, No. 12, pp. 1916-1923 (2002).
Torok et al., Applied and Environmental Microbiology, vol. 77, No. 17, pp. 5868-5878 (2011).

* cited by examiner

*Primary Examiner* — Padmavathi Baskar
(74) *Attorney, Agent, or Firm* — Elias Lambiris

(57) ABSTRACT

The present invention relates to methods of improving animal performance using animal feed comprising microbial polypeptides having lysozyme activity.

Figure 1:
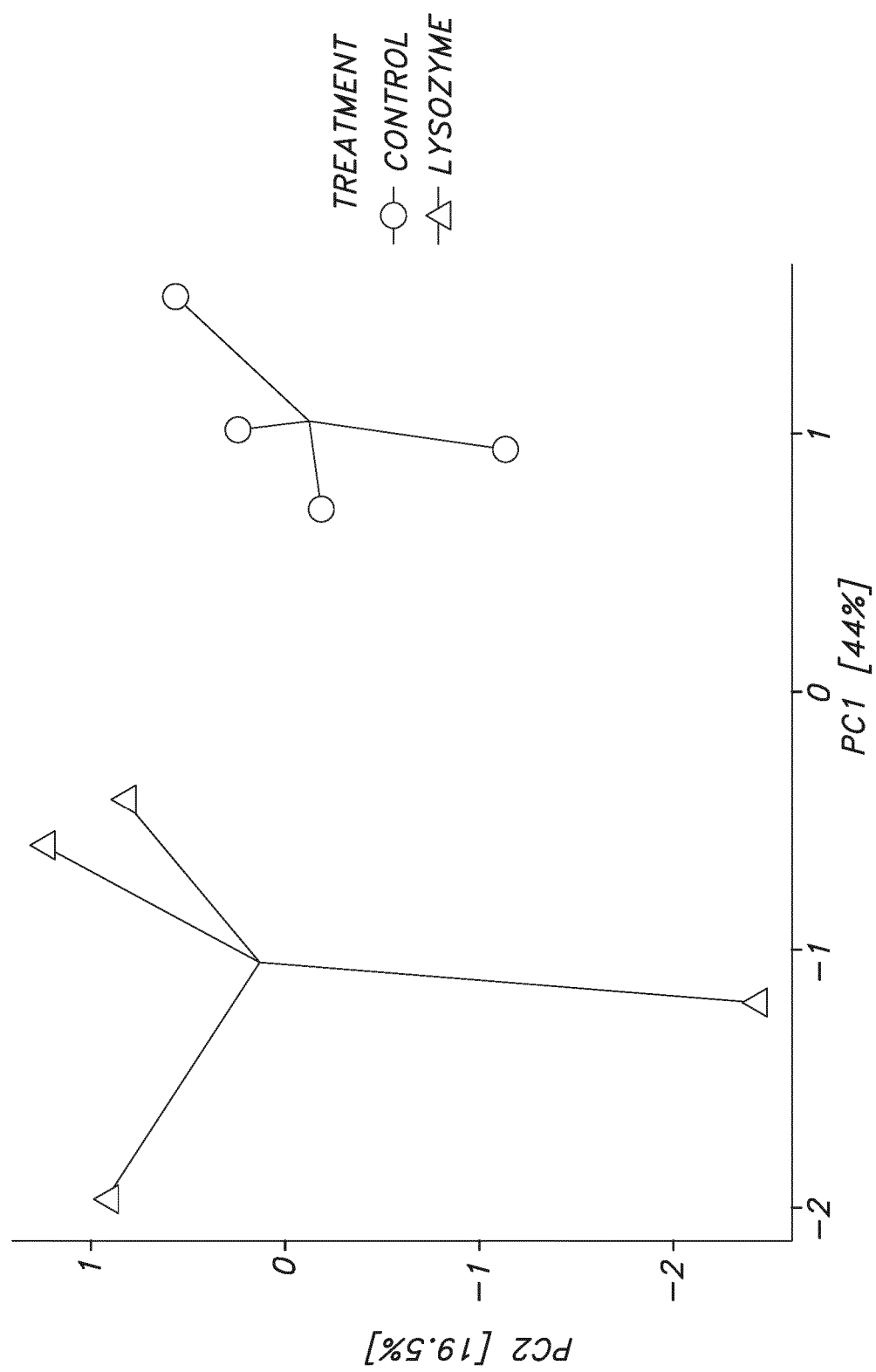

18 Claims, 4 Drawing Sheets
Specification includes a Sequence Listing.

METHODS OF IMPROVING ANIMAL PERFORMANCE

CROSS-REFERENCE TO RELATED APPLICATIONS

This application is a 35 U.S.C. 371 national application of international application no. PCT/EP2016/065701 filed Jul. 4, 2016, which claims priority or the benefit under 35 U.S.C. 119 of European application no. 15174930.6 filed Jul. 2, 2015. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to methods of improving animal performance using animal feed comprising microbial polypeptides having lysozyme activity.

Description of the Related Art

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse as a result of umbalanced osmotic pressure.

Lysozyme naturally occurs in many organisms such as viruses, plants, insects, birds, reptiles and mammals. In mammals, Lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25). Lysozymes from the families GH23 and GH24 are primarily known from bacteriophages and have only recently been identified in fungi. The lysozyme family GH25 has been found to be structurally unrelated to the other lysozyme families.

Lysozyme has traditionally been extracted from hen egg white due to its natural abundance and until very recently hen egg white lysozyme was the only lysozyme investigated for use in animal feed. Lysozyme extracted from hen egg white is the primary product available on the commercial market, but does not cleave N,6-O-diacetylmuramic acid in e.g. *Staphylococcus aureus* cell walls and is thus unable to lyse this important human pathogen among others (Masschalck B, Deckers D, Michiels C W (2002), "Lytic and nonlytic mechanism of inactivation of gram-positive bacteria by lysozyme under atmospheric and high hydrostatic pressure", *J Food Prot.* 65(12):1916-23).

WO2000/21381 discloses a composition comprising at least two antimicrobial enzymes and a polyunsaturated fatty acid, wherein one of the antimicrobial enzymes was a GH22 lysozyme from chicken egg white. GB2379166 discloses a composition comprising a compound that disrupts the peptidoglycan layer of bacteria and a compound that disrupts the phospholipid layer of bacteria, wherein the peptidoglycan disrupting compound was a GH22 lysozyme from chicken egg white.

WO2004/026334 discloses an antimicrobial composition for suppressing the growth of enteric pathogens in the gut of livestock comprising (a) a cell wall lysing substance or its salt, (b) a antimicrobial substance, (c) a sequestering agent and (d) a lantibiotic, wherein the cell wall lysing substance or its salt is a GH22 lysozyme from hen egg white.

The growing world population and increasing demand on animal protein reinforces the relevance of improving the growth performance of animals. Thus solutions which improve growth rate using less animal feed or resulting in bigger animals using the same amount of feed is always of interest to farmers. The object of this invention is to provide another solution to this global issue.

SUMMARY OF THE INVENTION

The invention relates to a method of improving the European Production Efficiency Factor (EPEF) and/or feed conversion ratio (FCR) of a monogastric animal comprising administering an animal feed or animal fee additive comprising one or more microbial lysozymes to the monogastric animal wherein the microbial lysozyme obtained or obtainable from the kingdom Fungi and is administered at a level of 8 to 250 ppm enzyme protein per kg animal feed.

The invention further relates to a method of increasing the proportion of bacteria of genus *Faecalibacterium* in the microbiome of the GI tract of a monogastric animal comprising administering to the animal an animal feed or animal feed additive comprising one or more microbial lysozymes administered at a level of 8 to 250 ppm enzyme protein per kg animal feed.

OVERVIEW OF SEQUENCE LISTING

SEQ ID NO: 1 is the mature amino acid sequence of a wild type GH25 lysozyme from *Acremonium alcalophilum* with N-terminal SPIRR as described in WO 2013/076253.

SEQ ID NO: 2 is the gene sequence of the GH24 lysozyme as isolated from *Trichophaea saccata*.

SEQ ID NO: 3 is the amino acid sequence as deduced from SEQ ID NO: 2.

SEQ ID NO: 4 is the mature amino acid sequence of a wild type GH24 lysozyme from *Trichophaea saccata*.

SEQ ID NO: 5 is the mature amino acid sequence of a wild type GH22 lysozyme from *Gallus gallus* (hen egg white lysozyme).

SEQ ID NO: 6 is primer F-80470.

SEQ ID NO: 7 is primer R-80470.

SEQ ID NO: 8 is primer 8643.

SEQ ID NO: 9 is primer 8654.

SEQ ID NO: 10 is the forward primer 27F.

SEQ ID NO: 11 is the reverse primer 534R.

SEQ ID NO: 12 is the mature amino acid sequence of a wild type GH25 lysozyme from *Acremonium alcalophilum* as described in WO 2013/076253.

SEQ ID NO: 13 is the sequence representing the V1-V3 region of the 16S rRNA gene in OTU_20 classified as the bacterial genus *Faecalibacterium* from in vivo trial 4 (Example 11).

SEQ ID NO: 14 is the sequence representing the V1-V3 region of the 16S rRNA gene in OTU_27 classified as the bacterial genus *Faecalibacterium* from in vivo trial 4 (Example 11).

SEQ ID NO: 15 is the sequence representing the V1-V3 region of the 16S rRNA gene in OTU_85 classified as the bacterial genus *Faecalibacterium* from in vivo trial 4 (Example 11).

FIGURES

FIG. 1: Principal component analysis plot showing a shift in the microbial composition in the chicken gut upon treatment with the lysozyme of SEQ ID NO: 1 at 50 ppm from in vivo broiler trial 4.

Figure 2:
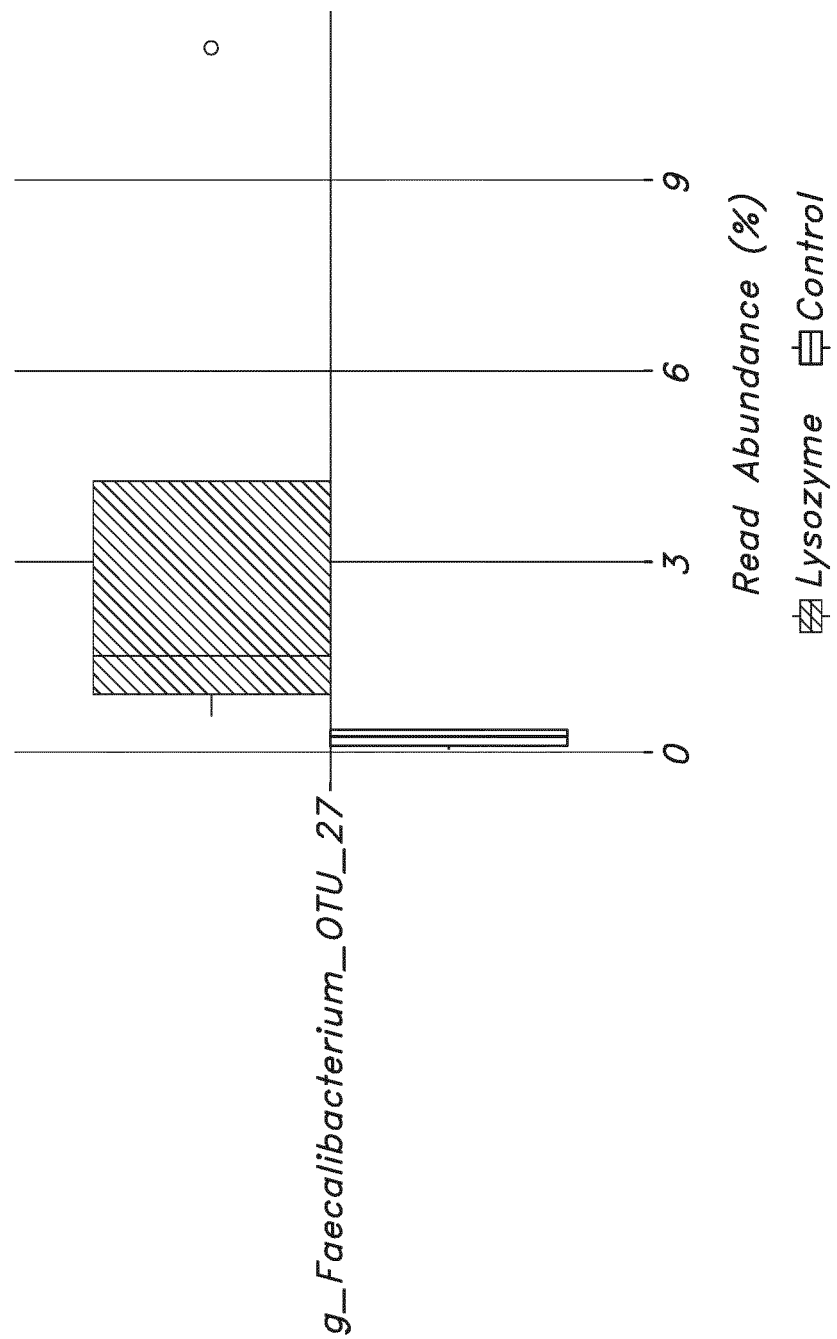

FIG. 2: Boxplot of observed changes in the composition of the chicken gut microbiota for in vivo broiler trial 4 (SEQ ID NO: 1 at 50 ppm) at OTU/species level. The boxplot was generated with the R programming language.

Figure 3:
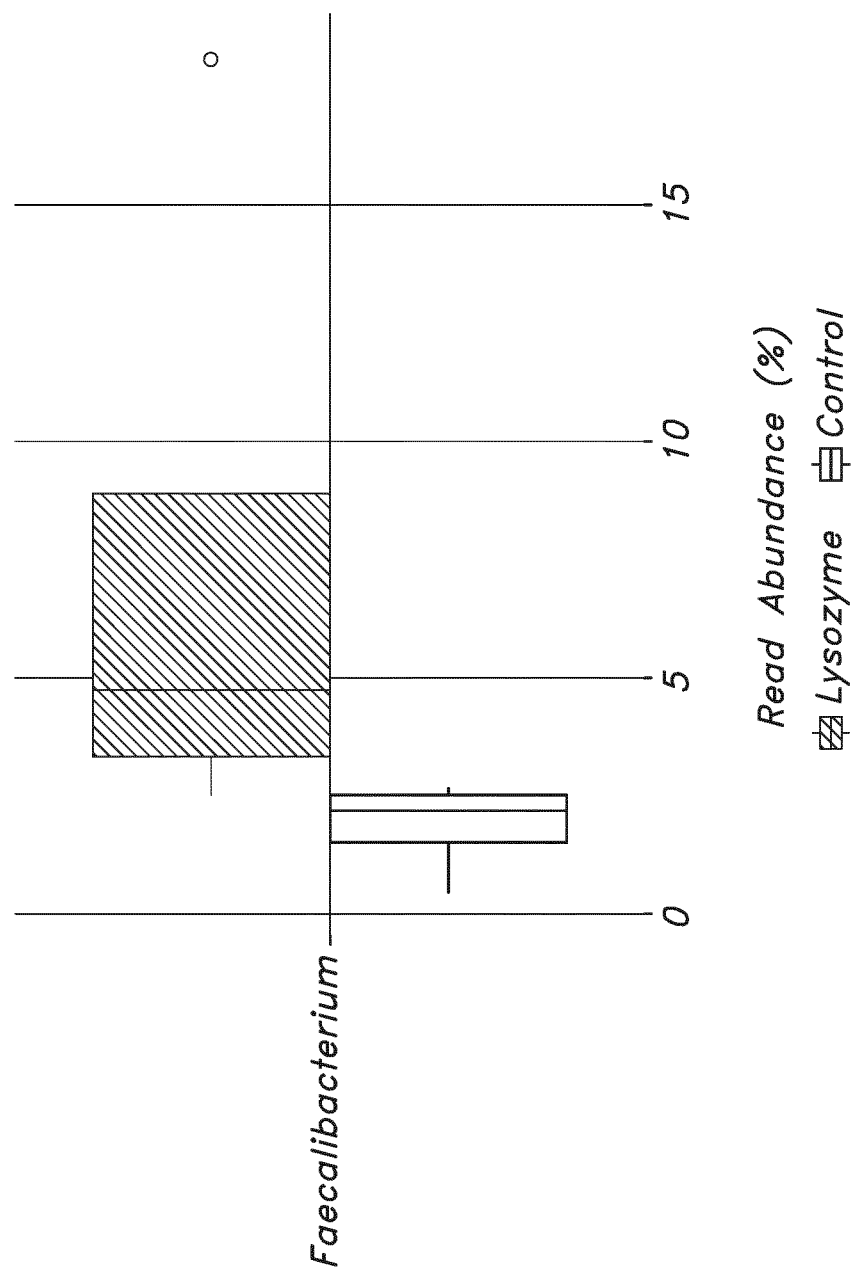

FIG. 3: Boxplot of observed changes in the composition of the chicken gut microbiota for in vivo broiler trial 4 (SEQ ID NO: 1 at 50 ppm) at genus level. The boxplot was generated with the R programming language.

Figure 4:
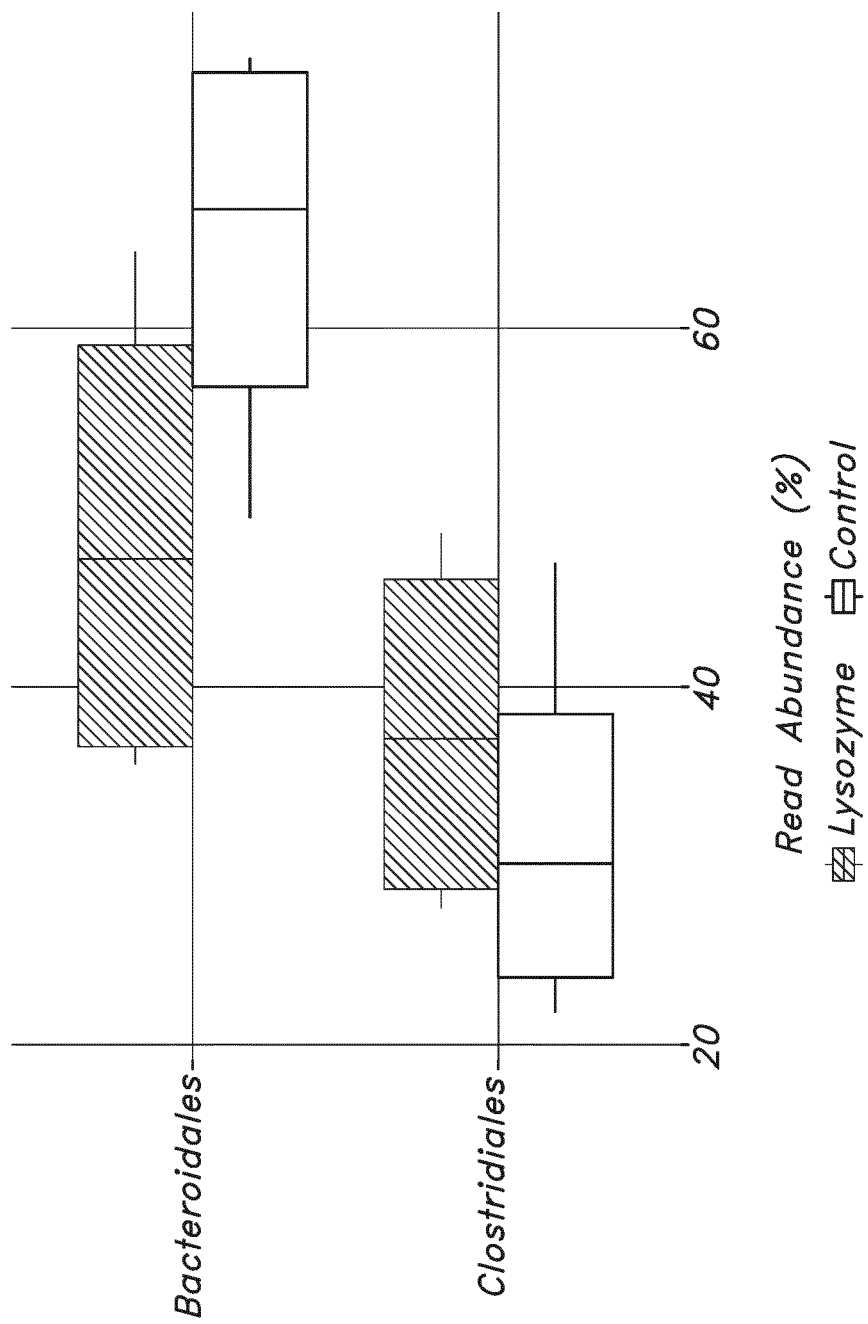

FIG. 4: Boxplot of observed changes in the composition of the chicken gut microbiota for in vivo broiler trial 4 (SEQ ID NO: 1 at 50 ppm) at order level. The boxplot was generated with the R programming language.

DEFINITIONS

Animal feed: The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Antimicrobial activity: The term "antimicrobial activity" is defined herein as an activity that kills or inhibits the growth of microorganisms, such as, algae, archea, bacteria, fungi and/or protozoans. The antimicrobial activity can, for example, be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the lysozyme binding to the surface of the microorganism and inhibiting its growth. The antimicrobial effect can also include the use of the lysozymes of the present invention for activation of bacterial autolysins, as an immunostimulator, by inhibiting or reducing bacterial toxins and by an opsonin effect.

For the purpose of the present invention, antimicrobial activity is determined according to the antimicrobial assay described in Example 6 ("Determination of antimicrobial activity"). Antimicrobial activity is determined if there is a clearning zone when using 50% Mueller-Hinton broth, pH 6. Preferably the diameter of the clearing zone is 4 mm or more.

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

European Production Efficiency Factor (EPEF): The European Production Efficiency Factor is a way of comparing the performance of animals. This single-figure facilitates comparison of performance within and among farms and can be used to assess environmental, climatic and animal management variables. The EPEF is calculated as [(liveability (%)×Liveweight (kg))/(Age at depletion (days)×FCR)]× 100, wherein livability is the percentage of animals alive at slaughter, Liveweight is the average weight of the animals at slaughter, age of depletion is the age of the animals at slaughter and FCR is the feed conversion ratio at slaughter.

*Faecalibacterium*: It is known (Větrovský T, Baldrian P (2013) The Variability of the 16S rRNA Gene in Bacterial Genomes and Its Consequences for Bacterial Community Analyses. PLoS ONE 8(2): e57923. doi: 10.1371/journal.pone.0057923) that the 16S rRNA gene sequence identity varies within a genus. It has been shown that the mean identity is 95.56 with a standard deviation of 3.68. It was also found that 12.2% of genera contain species with mean pairwise 16S rRNA gene similarity below 90%.

SEQ ID NO: 13 to 15 inclusive contains 16S rRNA gene sequences classified as genus *Faecalibacterium* from in vivo trial 4 (Example 11) where the V1-V3 region of the 16S rRNA gene was used for amplification. The classification was performed using the program "rdp classifier" v.2.2. OTU_20 (SEQ ID NO: 13) from in vivo trial 4 (Example 1) was the most abundant *Faecalibacterium* in this trial.

Thus strains are hereby defined as *Faecalibacterium* wherein the sequence identity of the V1-V3 region of the 16S rRNA gene of said strain has at least 90% e.g., at least 91%, at least 92%, at least 93%, at least 94%, at least 95%, at least 96%, at least 97%, at least 98%, at least 99%, or 100% sequence identity to one or more of SEQ ID NO: 13 to 15. Preferably the sequence identity of the V1-V3 region of the 16S rRNA gene of said strain has at least 90%, more preferably at least 93%, even more preferably at least 95%, even more preferably at least 96%, even more preferably at least 97%, even more preferably at least 98%, even more preferably at least 99%, or most preferably 100% sequence identity to SEQ ID NO: 13.

Feed Conversion Ratio (FCR): FCR is a measure of an animal's efficiency in converting feed mass into increases of the desired output. Animals raised for meat—such as swine, poultry and fish—the output is the mass gained by the animal. Specifically FCR is calculated as feed intake divided by weight gain, all over a specified period. Improvement in FCR means reduction of the FCR value. A FCR improvement of 2% means that the FCR was reduced by 2%.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, *brassica* (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide or a catalytic domain having one or more (e.g., several) amino acids absent from the amino and/or carboxyl terminus of a mature polypeptide or domain; wherein the fragment has lysozyme. In one aspect, a fragment comprises at least 170 amino acids, such as at least 175 amino acids, at least 177 amino acids, at least 180 amino acids, at least 185 amino acids, at least 190 amino acids, at least 195 amino acids or at least 200 amino acids of SEQ ID NO: 1 and has lysozyme activity.

In another aspect, a fragment comprises at least 210 amino acids, such as at least 215 amino acids, at least 220 amino acids, at least 225 amino acids, at least 230 amino acids, at least 235 amino acids or at least 240 amino acids of SEQ ID NO: 4 and has lysozyme activity.

In one aspect, a fragment comprises at least 170 amino acids, such as at least 175 amino acids, at least 177 amino acids, at least 180 amino acids, at least 185 amino acids, at least 190 amino acids, at least 195 amino acids or at least 200 amino acids of SEQ ID NO: 12 and has lysozyme activity.

Increases the proportion of bacteria of x in the microbiota of the GI tract of an animal: The term "increases the proportion of bacteria of x in the microbiota of the GI tract of an animal" means that the quantity of bacteria of a specific taxonomic rank (e.g. order or genus) has increased compared to a control sample. Samples of animal microbiota can be taken from the gut (i.e. gastrointestinal tract) of an animal (e.g. from broiler ceca or from the colon or ileum of swine) and analysed by examining the sequences (reads) of the 16S rRNA genes in the sample. The reads of the 16S rRNA genes can be clustered together based on sequence identity and each cluster can be compared to a database of known sequences of the 16S rRNA gene to identify the type of bacteria in that cluster. The clusters can be merged at different taxonomic levels (phylum, class, order, family, genus or species) to give a quantative analysis of the amount of bacteria within each taxonomy level over the entire sample By comparing the clusters from a control animal to an animal administered with a lysozyme of the invention, differences in the microbiota can be determined. Thus in one example, the proportion of bacteria of genus *Faecalibacterium* in the microbiota taken from broilers administered with a lysozyme of the invention increased from 0.22% to 3.67% (see table 9.2) compared to control (i.e. broilers not administered with a lysozyme). Thus in this example the proportion of bacteria of genus *Faecalibacterium* increased by 3.45%, which corresponds to an increase by a factor of 16.53.

In another example, the proportion of bacteria of order Clostridiales in the microbiota taken from broilers administered with a lysozyme of the invention increased from 32.1% to 37.6% (see table 9.4) compared to control. Thus in this example the proportion of bacteria of order Clostridiales decreased by 5.3%, which corresponds to an increase by a factor of 1.17.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Lysozyme activity: The term "lysozyme activity" means the enzymatic hydrolysis of the 1,4-beta-linkages between N-acetylmuramic acid and N-acetyl-D-glucosamine residues in a peptidoglycan or between N-acetyl-D-glucosamine residues in chitodextrins, resulting in bacteriolysis due to osmotic pressure. Lysozyme belongs to the enzyme class EC 3.2.1.17. Lysozyme activity is typically measured by turbidimetric determination. The method is based on the changes in turbidity of a suspension of *Micrococcus luteus* ATCC 4698 induced by the lytic action of lysozyme. In appropriate experimental conditions these changes are proportional to the amount of lysozyme in the medium (c.f. INS 1105 of the Combined Compendium of Food Additive Specifications of the Food and Agriculture Organisation of the UN (www-.fao.org)). For the purpose of the present invention, lysozyme activity is determined according to the turbidity assay described in example 5 ("Determination of Lysozyme Activity"). In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 1. In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 4. In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 12.

Mature polypeptide: The term "mature polypeptide" means a polypeptide in its final form following translation and any post-translational modifications, such as N-terminal processing, C-terminal truncation, glycosylation, phosphorylation, etc.

Microbial lysozyme: The term "microbial lysozyme" means a polypeptide having lysozyme activity which is obtained or obtainable from a microbial source. Examples of microbial sources are fungi; i.e. the lysozyme is obtained or obtainable from the kingdom Fungi, wherein the term kingdom is the taxonomic rank. In particular, the microbial lysozyme is obtained or obtainable from the phylum Ascomycota, such as the sub-phylum Pezizomycotina, wherein the terms phylum and sub-phylum is the taxonomic ranks.

If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Monogastric animal: The term "monogastric animal" refers to any animal which has a simple single-chambered stomach except humans. Examples of monogastric animals include pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Operational taxonomic unit (OTU): The term "Operational taxonomic unit" means a cluster of sequences with a certain degree of similarity. In this case, 97 percent is chosen as the threshold for assigning sequences of the 16S rRNA gene to different OTUs, meaning that all sequences within a single OTU have at least 97 percent sequence identity. At this identity level each OTU is often considered (or assumed) to represent a single bacterial species.

Roughage: The term "roughage" means dry plant material with high levels of fiber, such as fiber, bran, husks from seeds and grains and crop residues (such as stover, copra, straw, chaff, sugar beet waste).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, a lysozyme variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the lysozyme activity of the parent lysozyme, such as SEQ ID NO: 1, SEQ ID NO: 4 or SEQ ID NO: 12.

DETAILED DESCRIPTION OF THE INVENTION

Methods of Improving Animal Performance

It has been surprisingly found that supplementing an animal feed with a microbial lysozyme results in a significant performance benefit in monogastric animals, such as broilers and piglets, compared to an animal feed without the microbial lysozyme. This is surprising since improved animal performance using a microbial lysozyme has never previously been demonstrated.

It has furthermore been discovered that the microbiota of the GI tract of an animal, such as broilers, is significantly altered by administering a lysozyme of the invention. In one of the in vivo broiler trials, samples from the broiler ceca were taken for microbial community (microbiome) analysis and it was surprisingly discovered that:

(a) treatment with a GH25 lysozyme (SEQ ID NO: 1) leads to a higher proportion of a bacterial species of the genus *Faecalibacterium* in the chicken gut and this shift is associated with increased European Production Efficiency Factor (EPEF) in chickens and this bacterial species has 96% identity to the species *Faecalibacterium prausnitzii;*

(b) treatment with a GH25 lysozyme (SEQ ID NO: 1) leads to a higher proportion of bacteria of the genus *Faecalibacterium* in the chicken gut and this shift is associated with increased European Production Efficiency Factor (EPEF) in chickens;

(c) treatment with a GH25 lysozyme (SEQ ID NO: 1) leads to a higher proportion of bacteria of the order Clostridiales in the chicken gut and this shift is associated with increased European Production Efficiency Factor (EPEF) in chickens;

(d) treatment with a GH25 lysozyme (SEQ ID NO: 1) leads to a lower proportion of bacteria of the order Bacteroidales in the chicken gut and this shift is associated with increased European Production Efficiency Factor (EPEF) in chickens.

Treatment of chickens with a GH25 lysozyme (SEQ ID NO: 1) resulted in higher levels of bacteria within the genus *Faecalibacterium* in the chicken gut environment. The closest known species is *Faecalibacterium prausnitzii*, which is an obligate anaerobe rod-shapedbutyrate producing microorganism belonging to the phylum Firmicutes (Duncan et al. 2002, Int J Syst Evol Microbiol 52(Pt 6):2141-2146). It is abundant in the feces of several animal species (Haenen D, et al. "A diet high in resistant starch modulates microbiota composition, SOFA concentrations, and gene expression in pig intestine", J Nutr. 2013; 143: 274-283.; Lund M, Bjerrum L, Pedersen K. "Quantification of *Faecalibacterium prausnitzii*- and *Subdoligranulum* variable-like bacteria in the cecum of chickens by real-time PCR", Poult Sci. 2010; 89: 1217-1224). In humans, high levels of *F. prausnitzii* have been associated with obesity (Balamurugan R, et al "Quantitative differences in intestinal *Faecalibacterium prausnitzii* in obese Indian children", Br J Nutr. 2010; 103: 335-338), while a low abundance of *F. prausnitzii* has been linked to Inflammatory Bowel Disease (IBD, i.e. Crohn's disease (Sokol H, et al. "*Faecalibacterium prausnitzii* is an anti-inflammatory commensal bacterium identified by gut microbiota analysis of Crohn disease patients", Proc Natl Acad Sci USA. 2008; 105: 16731-16736) and ulcerative colitis (Machiels K, et al. "A decrease of the butyrate-producing species *Roseburia hominis* and *Faecalibacterium prausnitzii* defines dysbiosis in patients with ulcerative colitis", Gut. 2013. doi: 10.1136/gutjnl-2013-304833)).

Additionally, the butyrate produced by *F. prausnitzii* is both an energy source to enterocytes and act as an anti-inflammatory agent (Miguel S, et al. "Identification of metabolic signatures linked to anti-inflammatory effects of *Faecalibacterium prausnitzii*", MBio. 2015; 6:doi: 10.1128/mBio.00300-15bioinf). Thus without wishing to be bound by theory, it is believed that the GH25 lysozyme of the invention increase the proportion of butyrate producing bacteria (such as those from the order Clostridiales and specifically the genus *Faecalibacterium*).

Thus the invention relates to a method of improving the European Production Efficiency Factor (EPEF) and/or feed conversion ratio (FCR) of a monogastric animal comprising administering an animal feed or animal feed additive comprising one or more microbial lysozymes to the monogastric animal, wherein the microbial lysozyme is administered at a level of 8 to 250 ppm enzyme protein per kg animal feed.

In a preferred embodiment, the improvement is compared to an animal feed or animal feed additive wherein the microbial lysozyme is not present (herein referred to as the negative control).

In one embodiment, the EPEF is improved by at least 1%, such as by at least 1.5%, at least 2.0%, at least 2.5%, at least 3%, at least 3.5%, at least 4% or at least 5% compared to the control. In another embodiment, the EPEF is improved by between 1% and 15%, such as between 1% and 12%, between 1% and 10%, 1.5% and 8%, 2.0% and 7% compared to the control, or any combination of these intervals.

In one embodiment, the FCR is improved by at least 1%, such as by at least 1.25%, at least 1.5%, at least 1.75% or at least 2.0% compared to the control. In another embodiment, the FCR is improved by between 1% and 5%, such as between 1% and 4%, between 1% and 3%, 1.25% and 2.5%, 1.5% and 2% compared to the control, or any combination of these intervals.

In one embodiment, the microbial lysozyme is dosed at a level of 9 to 200 ppm enzyme protein per kg animal feed, such as 10 to 150 ppm, 11 to 125 ppm, 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the monogastric animal is a selected from the group consisting of swine, piglet, growing pig, sow, poultry, turkey, duck, quail, guinea fowl, goose, pigeon, squab, chicken, broiler, layer, pullet and chick, horse, crustaceans, shrimps, prawns, fish, amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish. In a preferred embodiment, the monogastric animal is a selected from the group consisting of swine, piglet, growing pig, sow, poultry, turkey, duck, quail, guinea fowl, goose, pigeon, squab, chicken, broiler, layer, pullet and chick. In a more preferred embodiment, the monogastric animal is a selected from the group consisting of swine, piglet, growing pig, sow, chicken, broiler, layer, and chick.

In one embodiment, the microbial lysozyme has antimicrobial activity towards *Clostridium perfringens*. In an embodiment, the microbial lysozyme has at least 60%, at least 70%, at least 80%, at least 85%, at least 90%, at least 95% or at least 100% of the antimicrobial activity of SEQ ID NO: 1 against *Clostridium perfringens* under the conditions 50% MHB, pH 6. In an embodiment, the microbial lysozyme has at least 60%, at least 70%, at least 80%, at least 85%, at least 90%, at least 95% or at least 100% of the antimicrobial activity of SEQ ID NO: 4 against *Clostridium perfringens* under the conditions 50% MHB, pH 6. In an embodiment, the microbial lysozyme has at least 60%, at least 70%, at least 80%, at least 85%, at least 90%, at least 95% or at least 100% of the antimicrobial activity of SEQ ID NO: 12 against *Clostridium perfringens* under the conditions 50% MHB, pH 6. Antimicrobial activity towards *Clostridium perfringens* can be determined according to the antimicrobial assay described in Example 6.

In another embodiment, the invention relates to a composition comprising a microbial lysozyme for the treatment of *Clostridium perfringens* in a monogastric animal wherein the composition improves the European Production Efficiency Factor (EPEF) and/or feed conversion ratio (FCR) of the monogastric animal.

In one embodiment, the microbial lysozyme is fed to the animal from birth until slaughter. In a preferred embodiment the microbial lysozyme is fed to the animal on a daily basis from birth until slaughter. In another preferred embodiment the microbial lysozyme is fed to the animal on a daily basis for at least 10 days, such as at least 15 days or at least 20 days (where the days can be continuous or non-continuous) during the life span of the animal. In embodiment, the microbial lysozyme is fed to the animal for 10-20 days followed by a non-treatment period of 5-10 days, and this cycle is repeated during the life span of the animal.

In a further embodiment, the microbial lysozyme is fed to broilers for the first 49 days after hatching. In a further embodiment, the microbial lysozyme is fed to broilers for the first 36 days after hatching. In a further embodiment, the microbial lysozyme is fed to broilers on days 22 to 36 after hatching. In a further embodiment, the microbial lysozyme is fed to broilers during the pre-starter (days 1-7) period. In a further embodiment, the microbial lysozyme is fed to broilers during the starter (days 8-22) period. In a further embodiment, the microbial lysozyme is fed to broilers during the pre-starter (days 1-7) and starter (days 8-22) period.

In a further embodiment, the microbial lysozyme is fed to layers during the life span of the animal. In a further embodiment, the microbial lysozyme is fed to layers for 76 weeks from hatching. In a further embodiment, the microbial lysozyme is fed to layers during the laying period, (from ca. week 18). In a further embodiment, the microbial lysozyme is fed to layers during the laying period but withheld during the forced molting period.

In a further embodiment, the microbial lysozyme is fed to turkeys during life span of the animal. In a further embodiment, the microbial lysozyme is fed to turkeys for 24 weeks from hatching. In a further embodiment, the microbial lysozyme is fed to turkeys for the first 16 weeks from hatching (for hens) and for the first 20 weeks for hatching (for toms).

In a further embodiment, the microbial lysozyme is fed to swine during life span of the animal. In a further embodiment, the microbial lysozyme is fed to swine for 27 weeks from birth. In a further embodiment, the microbial lysozyme is fed to piglets from birth to weaning (at 4 weeks). In a further embodiment, the microbial lysozyme is fed to piglets for the first 6 weeks from birth (4 weeks of lactation and 2 weeks post-weaning). In a further embodiment, the microbial lysozyme is fed to weaning piglets during the pre-starter (days 1-14 after weaning). In a further embodiment, the microbial lysozyme is fed to weaning piglets during the starter (days 15-42 after weaning) period. In a further embodiment, the microbial lysozyme is fed to weaning piglets during the pre-starter (days 1-14 after weaning) and starter (days 15-42 after weaning) period. In a further embodiment, the microbial lysozyme is fed to swine during the grower/fattening period (week 10 to ca. week 27 after birth).

In one embodiment, the microbial lysozyme is of fungal origin. In an embodiment, the microbial lysozyme is obtained or obtainable from the phylum Ascomycota, such as the sub-phylum Pezizomycotina.

In one embodiment, the microbial lysozyme comprises one or more domains selected from the list consisting of GH24 and GH25.

In one embodiment, the method further increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 3%, at least 4% or at least 5%. In an alternative embodiment, the proportion of bacteria of genus *Faecalibacterium* is increased by a factor of at least 1.25, such as at least 1.50, at least 1.75, at least 2.0, at least 2.5 or at least 3.0.

In one embodiment, the method improves the European Production Efficiency Factor (EPEF) of an animal by at least 1% and increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 3%, at least 4% or at least 5% and the EPEF is increased by at least 1.25%, preferably by at least 1.5%, at least 1.75%, at least 2%, at least 3%, at least 4% or most preferably by at least 5%.

In one embodiment, the method improves the European Production Efficiency Factor (EPEF) of an animal by at least 1% and increases the proportion of bacteria of genus *Faecalibacterium* in the microbiota of the GI tract of an animal. In an embodiment, the proportion of bacteria of genus *Faecalibacterium* is increased by factor of at least 1.25, such as at least 1.50, at least 1.75, at least 2.0, at least 2.5 or at least 3.0 and the EPEF is increased by at least 1.25%, preferably by at least 1.5%, at least 1.75%, at least 2%, at least 3%, at least 4% or most preferably by at least 5%.

In one embodiment, the method improves the Feed Conversion Ratio (FCR) of an animal by at least 1% and increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 3%, at least 4% or at least 5% and the FCR is increased by at least 1.25%, preferably by at least 1.5% or most preferably by at least 1.75%.

In one embodiment, the method improves the Feed Conversion Ratio (FCR) of an animal by at least 1% and increases the proportion of bacteria of genus *Faecalibacterium* in the microbiota of the GI tract of an animal. In an embodiment, the proportion of bacteria of genus *Faecalibacterium* is increased by factor of at least 1.25, such as at least 1.50, at least 1.75, at least 2.0, at least 2.5 or at least 3.0 and the FCR is increased by at least 1.25%, preferably by at least 1.5% or most preferably by at least 1.75%.

In one embodiment, the method further increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by at least 1%, such as at least 2%, at least 3%, at least 4% or at least 5%. In an alternative embodiment, the proportion of bacteria of genus *Faecalibacterium* is increased by a factor of at least 1.25, such as at least 1.50, at least 1.75, at least 2.0, at least 2.5 or at least 3.0.

In one embodiment, the method improves the European Production Efficiency Factor (EPEF) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by at least 1%, such as at least 2%, at least 3%, at least 4% or at least 5% and the EPEF is increased by at least 1.25%, preferably by at least 1.5%, at least 1.75%, at least 2%, at least 3%, at least 4% or most preferably by at least 5%.

In one embodiment, the method improves the European Production Efficiency Factor (EPEF) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by factor of at least 1.25, such as at least 1.50, at least 1.75, at least 2.0, at least 2.5 or at least 3.0 and the EPEF is increased by at least 1.25%, preferably by at least 1.5%, at least 1.75%, at least 2%, at least 3%, at least 4% or most preferably by at least 5%.

In one embodiment, the method improves the Feed Conversion Ratio (FCR) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by at least 1%, such as at least 2%, at least 3%, at least 4% or at least 5% and the FCR is increased by at least 1.25%, preferably by at least 1.5% or most preferably by at least 1.75%.

In one embodiment, the method improves the Feed Conversion Ratio (FCR) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by factor of at least 1.25, such as at least 1.50, at least 1.75, at least 2.0, at least 2.5 or at least 3.0 and the FCR is increased by at least 1.25%, preferably by at least 1.5% or most preferably by at least 1.75%.

In a preferred embodiment, the invention relates to a method of improving the European Production Efficiency Factor (EPEF) and/or feed conversion ratio (FCR) of a monogastric animal comprising administering an animal feed or animal feed additive comprising one or more microbial lysozymes to the monogastric animal, wherein:

(a) the microbial lysozyme is a microbial lysozyme comprising one or more domains selected from the list consisting of GH24 and GH25, is dosed at a level of 10 to 150 ppm enzyme protein per kg animal feed and has antimicrobial activity towards *Clostridium perfringens*;

(b) the monogastric animal is a selected from the group consisting of swine, piglet, growing pig, sow, chicken, broiler, layer, pullet and chick;

(c) European Production Efficiency Factor (EPEF) and/or feed conversion ratio (FCR) is improved by at least 1% compared to control; and (d) optionally the microbial lysozyme is fed to the monogastric animal on a daily basis for at least 10 days during the life span of the animal.

In one embodiment, the microbial lysozyme has at least 60%, at least 70%, at least 80%, at least 85%, at least 90%, at least 95% or at least 100% of the antimicrobial activity of SEQ ID NO: 1 against *Clostridium perfringens* under the conditions 50% MHB, pH 6. In another embodiment, the microbial lysozyme has at least 60%, at least 70%, at least 80%, at least 85%, at least 90%, at least 95% or at least 100% of the antimicrobial activity of SEQ ID NO: 4 against *Clostridium perfringens* under the conditions 50% MHB, pH 6. In another embodiment, the microbial lysozyme has at least 60%, at least 70%, at least 80%, at least 85%, at least 90%, at least 95% or at least 100% of the antimicrobial activity of SEQ ID NO: 12 against *Clostridium perfringens* under the conditions 50% MHB, pH 6.

In one embodiment, the EPEF is improved by at least 1.5%, such as by at least 2.0%, at least 2.5%, at least 3%, at least 3.5%, at least 4% or at least 5% compared to the control. In another embodiment, the EPEF is improved by between 1% and 15%, such as between 1% and 12%, between 1% and 10%, 1.5% and 8%, 2.0% and 7% compared to the control, or any combination of these intervals.

In one embodiment, the FCR is improved by at least 1.25%, such as by at least 1.5%, at least 1.75% or at least 2.0% compared to the control. In another embodiment, the FCR is improved by between 1% and 5%, such as between 1% and 4%, between 1% and 3%, 1.25% and 2.5%, 1.5% and 2% compared to the control, or any combination of these intervals.

In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the microbial lysozyme is fed to the animal from birth until slaughter. In a preferred embodiment the microbial lysozyme is fed to the animal on a daily basis from birth until slaughter. In another preferred embodiment the microbial lysozyme is fed to the animal on a daily basis for at least 10 days, such as at least 15 days or at least 20 days (where the days can be continuous or non-continuous) during the life span of the animal. In embodiment, the microbial lysozyme is fed to the animal for 10-20 days followed by a non-treatment period of 5-10 days, and this cycle is repeated during the life span of the animal.

In a further embodiment, the microbial lysozyme is fed to broilers for the first 49 days after hatching. In a further embodiment, the microbial lysozyme is fed to broilers for the first 36 days after hatching. In a further embodiment, the microbial lysozyme is fed to broilers on days 22 to 36 after hatching. In a further embodiment, the microbial lysozyme is fed to broilers during the pre-starter (days 1-7) period. In a further embodiment, the microbial lysozyme is fed to broilers during the starter (days 8-22) period. In a further embodiment, the microbial lysozyme is fed to broilers during the pre-starter (days 1-7) and starter (days 8-22) period.

In a further embodiment, the microbial lysozyme is fed to layers during the life span of the animal. In a further embodiment, the microbial lysozyme is fed to layers for 76 weeks from hatching. In a further embodiment, the microbial lysozyme is fed to layers during the laying period, (from ca. week 18). In a further embodiment, the microbial lysozyme is fed to layers during the laying period but withheld during the forced molting period.

In a further embodiment, the microbial lysozyme is fed to turkeys during life span of the animal. In a further embodiment, the microbial lysozyme is fed to turkeys for 24 weeks from hatching. In a further embodiment, the microbial lysozyme is fed to turkeys for the first 16 weeks from hatching (for hens) and for the first 20 weeks for hatching (for toms).

In a further embodiment, the microbial lysozyme is fed to swine during life span of the animal. In a further embodiment, the microbial lysozyme is fed to swine for 27 weeks from birth. In a further embodiment, the microbial lysozyme is fed to piglets from birth to weaning (at 4 weeks).

In a further embodiment, the microbial lysozyme is fed to piglets for the first 6 weeks from birth (4 weeks of lactation and 2 weeks post-weaning). In a further embodiment, the microbial lysozyme is fed to weaning piglets during the pre-starter (days 1-14 after weaning). In a further embodiment, the microbial lysozyme is fed to weaning piglets during the starter (days 15-42 after weaning) period. In a further embodiment, the microbial lysozyme is fed to weaning piglets during the pre-starter (days 1-14 after weaning) and starter (days 15-42 after weaning) period. In a further embodiment, the microbial lysozyme is fed to swine during the grower/fattening period (week 10 to ca. week 27 after birth).

In one embodiment, the microbial lysozyme is of fungal origin. In an embodiment, the microbial lysozyme is obtained or obtainable from the phylum Ascomycota, such as the sub-phylum Pezizomycotina.

In one embodiment, the microbial lysozyme has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1.

In one embodiment, the microbial lysozyme comprises or consists of the amino acid sequence of SEQ ID NO: 1 or an allelic variant thereof; or is a fragment thereof having lysozyme activity, wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids. In another embodiment, the microbial lysozyme comprises or consists of the amino acid sequence of SEQ ID NO: 1 or an allelic variant thereof and a N-terminal and/or C-terminal His-tag and/or HQ-tag. In another aspect, the polypeptide comprises or consists of amino acids 1 to 213 of SEQ ID NO: 1.

In another embodiment, the microbial lysozyme is a variant of SEQ ID NO: 1 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 1 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 1 is not more than 10, e.g., 1, 2, 3, 4, 5, 6, 7, 8, 9 or 10. In another embodiment, the number of substitutions, deletions, and/or insertions in SEQ ID NO: 1 is not more than 10, e.g., 1, 2, 3, 4, 5, 6, 7, 8, 9 or 10. In a further embodiment, the number of substitutions, preferably conservative substitutions, in SEQ ID NO: 1 is not more than 10, e.g., 1, 2, 3, 4, 5, 6, 7, 8, 9 or 10. In a further embodiment, the number of conservative substitutions in SEQ ID NO: 1 is not more than 10, e.g., 1, 2, 3, 4, 5, 6, 7, 8, 9 or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The crystal structure of the *Acremonium alcalophilum* CBS114.92 lysozyme was solved at a resolution of 1.3 Å as disclosed in WO 2013/076253. These atomic coordinates can be used to generate a three dimensional model depicting the structure of the *Acremonium alcalophilum* CBS114.92 lysozyme or homologous structures (such as the variants of the present invention). Using the x/ray structure, amino acid residues D95 and E97 (using SEQ ID NO: 1 for numbering) were identified as catalytic residues.

In one embodiment, the microbial lysozyme has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4.

In one embodiment, the microbial lysozyme comprises or consists of the amino acid sequence of SEQ ID NO: 4 or an allelic variant thereof; or is a fragment thereof having lysozyme activity, wherein the fragment comprises at least 210 amino acids, such as at least 215 amino acids, at least 220 amino acids, at least 225 amino acids, at least 230 amino acids, at least 235 amino acids or at least 240 amino acids. In another embodiment, the microbial lysozyme comprises or consists of the amino acid sequence of SEQ ID NO: 4 or an allelic variant thereof and a N-terminal and/or C-terminal His-tag and/or HQ-tag. In another aspect, the polypeptide comprises or consists of amino acids 1 to 245 of SEQ ID NO: 4.

In another embodiment, the microbial lysozyme is a variant of SEQ ID NO: 4 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 4 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 4 is not more than 10, e.g., 1, 2, 3, 4, 5, 6, 7, 8, 9 or 10. In another embodiment, the number of substitutions, deletions, and/or insertions in SEQ ID NO: 4 is not more than 10, e.g., 1, 2, 3, 4, 5, 6, 7, 8, 9 or 10. In a further embodiment, the number of substitutions, preferably conservative substitutions, in SEQ ID NO: 4 is not more than 10, e.g., 1, 2, 3, 4, 5, 6, 7, 8, 9 or 10. In a further embodiment, the number of conservative substitutions in SEQ ID NO: 4 is not more than 10, e.g., 1, 2, 3, 4, 5, 6, 7, 8, 9 or 10.

Examples of amino acid changes, conservative substitutions and N- and/or C-terminal linkers are described above.

In one embodiment, the microbial lysozyme has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12.

In one embodiment, the microbial lysozyme comprises or consists of the amino acid sequence of SEQ ID NO: 12 or an allelic variant thereof; or is a fragment thereof having lysozyme activity, wherein the fragment comprises at least 210 amino acids, such as at least 215 amino acids, at least 220 amino acids, at least 225 amino acids, at least 230 amino acids, at least 235 amino acids or at least 240 amino acids. In another embodiment, the microbial lysozyme comprises or consists of the amino acid sequence of SEQ ID NO: 12 or an allelic variant thereof and a N-terminal and/or C-terminal His-tag and/or HQ-tag. In another aspect, the polypeptide comprises or consists of amino acids 1 to 208 of SEQ ID NO: 12.

In another embodiment, the microbial lysozyme is a variant of SEQ ID NO: 12 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 12 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In another embodiment, the number of substitutions, deletions, and/or insertions in SEQ ID NO: 12 is not more than 10, e.g., 1, 2, 3, 4, 5, 6, 7, 8, 9 or 10. In a further embodiment, the number of substitutions, preferably conservative substitutions, in SEQ ID NO: 12 is not more than 10, e.g., 1, 2, 3, 4, 5, 6, 7, 8, 9 or 10. In a further embodiment, the number of conservative substitutions in SEQ ID NO: 12 is not more than 10, e.g., 1, 2, 3, 4, 5, 6, 7, 8, 9 or 10.

Examples of amino acid changes, conservative substitutions and N- and/or C-terminal linkers are described above.

In another preferred embodiment, the invention relates to a method of improving the European Production Efficiency Factor (EPEF) and/or feed conversion ratio (FCR) of a monogastric animal comprising administering an animal feed or animal feed additive comprising one or more microbial lysozymes to the monogastric animal, wherein:

(a) the microbial lysozyme is a GH24 lysozyme obtained or obtainable from the phylum Ascomycota, is dosed at a level of 10 to 150 ppm enzyme protein per kg animal feed and has antimicrobial activity towards *Clostridium perfringens;*

(b) the monogastric animal is a selected from the group consisting of swine, piglet, growing pig, sow, chicken, broiler, layer, pullet and chick;

(c) European Production Efficiency Factor (EPEF) and/or feed conversion ratio (FCR) is improved by at least 1% compared to control; and (d) the proportion of bacteria of genus *Faecalibacterium* in the microbiota of the GI tract of an animal is increased by at least 1%.

In one embodiment, the EPEF is improved by at least 1.5%, such as by at least 2.0%, at least 2.5%, at least 3%, at least 3.5%, at least 4% or at least 5% and the proportion of bacteria of genus *Faecalibacterium* is increased by at least 2%, such as at least 3%, at least 4% or at least 5% compared to the control.

In one embodiment, the FCR is improved by at least 1.25%, such as by at least 1.5%, at least 1.75% or at least 2.0% and the proportion of bacteria of genus *Faecalibacterium* is increased by at least 2%, such as at least 3%, at least 4% or at least 5% compared to the control.

In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the microbial lysozyme is fed to the animal using one of the regimes as disclosed herein.

In another preferred embodiment, the invention relates to a method of improving the European Production Efficiency Factor (EPEF) and/or feed conversion ratio (FCR) of a monogastric animal comprising administering an animal feed or animal feed additive comprising one or more microbial lysozymes to the monogastric animal, wherein:

(a) the microbial lysozyme is a GH24 lysozyme obtained or obtainable from the phylum Ascomycota, is dosed at a level of 10 to 150 ppm enzyme protein per kg animal feed and has antimicrobial activity towards *Clostridium perfringens;*

(b) the monogastric animal is a selected from the group consisting of swine, piglet, growing pig, sow, chicken, broiler, layer, pullet and chick;

(c) European Production Efficiency Factor (EPEF) and/or feed conversion ratio (FCR) is improved by at least 1% compared to control; and (d) the proportion of bacteria of genus *Faecalibacterium* in the microbiota of the GI tract of an animal is increased by a factor of at least 1.25.

In one embodiment, the EPEF is improved by at least 1.5%, such as by at least 2.0%, at least 2.5%, at least 3%, at least 3.5%, at least 4% or at least 5% and the proportion of bacteria of genus *Faecalibacterium* is increased by a factor of at least 1.50, such as at least 1.75, at least 2.0, at least 2.5 or at least 3.0 compared to the control.

In one embodiment, the FCR is improved by at least 1.25%, such as by at least 1.5%, at least 1.75% or at least 2.0% and the proportion of bacteria of genus *Faecalibacte-*

*rium* is increased by a factor of at least 1.50, such as at least 1.75, at least 2.0, at least 2.5 or at least 3.0 compared to the control.

In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the microbial lysozyme is fed to the animal using one of the regimes as disclosed herein.

In another preferred embodiment, the invention relates to a method of improving the European Production Efficiency Factor (EPEF) and/or feed conversion ratio (FCR) of a monogastric animal comprising administering an animal feed or animal feed additive comprising one or more microbial lysozymes to the monogastric animal, wherein:

(a) the microbial lysozyme is a GH25 lysozyme obtained or obtainable from the phylum Ascomycota, is dosed at a level of 10 to 150 ppm enzyme protein per kg animal feed and has antimicrobial activity towards *Clostridium perfringens*;

(b) the monogastric animal is a selected from the group consisting of swine, piglet, growing pig, sow, chicken, broiler, layer, pullet and chick;

(c) European Production Efficiency Factor (EPEF) and/or feed conversion ratio (FCR) is improved by at least 1% compared to control; and (d) the proportion of bacteria of genus *Faecalibacterium* in the microbiota of the GI tract of an animal is increased by at least 1%.

In one embodiment, the EPEF is improved by at least 1.5%, such as by at least 2.0%, at least 2.5%, at least 3%, at least 3.5%, at least 4% or at least 5% and the proportion of bacteria of genus *Faecalibacterium* is increased by at least 2%, such as at least 3%, at least 4% or at least 5% compared to the control.

In one embodiment, the FCR is improved by at least 1.25%, such as by at least 1.5%, at least 1.75% or at least 2.0% and the proportion of bacteria of genus *Faecalibacterium* is increased by at least 2%, such as at least 3%, at least 4% or at least 5% compared to the control.

In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the microbial lysozyme is fed to the animal using one of the regimes as disclosed herein.

In another preferred embodiment, the invention relates to a method of improving the European Production Efficiency Factor (EPEF) and/or feed conversion ratio (FCR) of a monogastric animal comprising administering an animal feed or animal feed additive comprising one or more microbial lysozymes to the monogastric animal, wherein:

(a) the microbial lysozyme is a GH25 lysozyme obtained or obtainable from the phylum Ascomycota, is dosed at a level of 10 to 150 ppm enzyme protein per kg animal feed and has antimicrobial activity towards *Clostridium perfringens*;

(b) the monogastric animal is a selected from the group consisting of swine, piglet, growing pig, sow, chicken, broiler, layer, pullet and chick;

(c) European Production Efficiency Factor (EPEF) and/or feed conversion ratio (FCR) is improved by at least 1% compared to control; and (d) the proportion of bacteria of genus *Faecalibacterium* in the microbiota of the GI tract of an animal is increased by a factor of at least 1.25.

In one embodiment, the EPEF is improved by at least 1.5%, such as by at least 2.0%, at least 2.5%, at least 3%, at least 3.5%, at least 4% or at least 5% and the proportion of bacteria of genus *Faecalibacterium* is increased by a factor of at least 1.50, such as at least 1.75, at least 2.0, at least 2.5 or at least 3.0 compared to the control.

In one embodiment, the FCR is improved by at least 1.25%, such as by at least 1.5%, at least 1.75% or at least 2.0% and the proportion of bacteria of genus *Faecalibacterium* is increased by a factor of at least 1.50, such as at least 1.75, at least 2.0, at least 2.5 or at least 3.0 compared to the control.

In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the microbial lysozyme is fed to the animal using one of the regimes as disclosed herein.

Formulating Agent

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate. The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In an embodiment, the solid composition is in granulated form. The granule may have a matrix structure where the components are mixed homogeneously. However, the granule typically comprises a core particle and one or more coatings, which typically are salt and/or wax coatings. Examples of waxes are polyethylene glycols; polypropylenes; Carnauba wax; Candelilla wax; bees wax; hydrogenated plant oil or animal tallow such as hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; micro-crystalline wax; paraffin's; and fatty acids, such as hydrogenated linear long chained fatty acids and derivatives thereof. A preferred wax is palm oil or hydrogenated palm oil. The core particle can either be a homogeneous blend of lysozyme of the invention optionally combined with one or more additional enzymes and optionally together with one or more salts or an inert particle with the lysozyme of the invention optionally combined with one or more additional enzymes applied onto it.

In an embodiment, the material of the core particles are selected from the group consisting of inorganic salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In a preferred embodiment, the core comprises a clay mineral such as kaolinite or kaolin.

The salt coating is typically at least 1 μm thick and can either be one particular salt or a mixture of salts, such as $Na_2SO_4$, $K_2SO_4$, $MgSO_4$ and/or sodium citrate. Other examples are those described in e.g. WO 2008/017659, WO 2006/034710, WO 1997/05245, WO 1998/54980, WO 1998/55599, WO 2000/70034 or polymer coating such as described in WO 2001/00042.

In another embodiment, the composition is a solid composition comprising the lysozyme of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate and calcium carbonate. In a preferred embodiment, the solid composition is in granulated form. In an embodiment, the solid composition is in granulated form and comprises a core particle, an enzyme layer comprising the lysozyme of the invention and a salt coating.

In a further embodiment, the formulating agent is selected from one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose. In a preferred embodiment, the formulating agent is selected from one or more of the following compounds: 1, 2-propylene glycol, 1, 3-propylene glycol, sodium sulfate, dextrin, cellulose, sodium thiosulfate, kaolin and calcium carbonate.

Animal Feed and Animal Feed Additives

Animal feed compositions or diets have a relatively high content of protein. Poultry and pig diets can be characterised as indicated in Table B of WO 2001/058275, columns 2-3. Fish diets can be characterised as indicated in column 4 of this Table B. Furthermore such fish diets usually have a crude fat content of 200-310 g/kg.

An animal feed composition according to the invention has a crude protein content of between 50 and 800 g/kg, and furthermore comprises one or more polypeptides having lysozyme activity as described herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 2001/058275 (R. 2-5).

The nitrogen content is determined by the Kjeldahl method (A.O.A.C., 1984, Official Methods of Analysis 14th ed., Association of Official Analytical Chemists, Washington D.C.) and crude protein is calculated as nitrogen (N) multiplied by a factor 6.25 (i.e. Crude protein (g/kg)=N (g/kg)× 6.25).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically a liquid enzyme preparation comprises the lysozyme of the invention optionally with a polyol, such as glycerol, ethylene glycol or propylene glycol, and is added after the pelleting step, such as by spraying the liquid formulation onto the pellets. The lysozyme may also be incorporated in a feed additive or premix.

Alternatively, the lysozyme can be prepared by freezing a mixture of liquid enzyme solution with a bulking agent such as ground soybean meal, and then lyophilizing the mixture.

In an embodiment, the composition comprises one or more additional enzymes. In an embodiment, the composition comprises one or more microbes. In an embodiment, the composition comprises one or more vitamins. In an embodiment, the composition comprises one or more minerals. In an embodiment, the composition comprises one or more amino acids. In an embodiment, the composition comprises one or more other feed ingredients.

In another embodiment, the composition comprises one or more of the polypeptides of the invention, one or more formulating agents and one or more additional enzymes. In an embodiment, the composition comprises one or more of the polypeptides of the invention, one or more formulating agents and one or more microbes. In an embodiment, the composition comprises one or more of the polypeptides of the invention, one or more formulating agents and one or more vitamins. In an embodiment, the composition comprises one or more of the polypeptides of the invention and one or more minerals. In an embodiment, the composition comprises the polypeptide of the invention, one or more formulating agents and one or more amino acids. In an embodiment, the composition comprises one or more of the polypeptides of the invention, one or more formulating agents and one or more other feed ingredients.

In a further embodiment, the composition comprises one or more of the polypeptides of the invention, one or more formulating agents and one or more components selected from the list consisting of: one or more additional enzymes; one or more microbes; one or more vitamins; one or more minerals; one or more amino acids; and one or more other feed ingredients.

The final lysozyme concentration in the diet is within the range of 0.01-200 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm or 10 to 30 ppm enzyme protein per kg animal feed, or any combination of these intervals.

It is at present contemplated that the lysozyme is administered in one or more of the following amounts (dosage ranges): 0.01-200; 0.01-100; 0.5-100; 1-50; 5-100; 5-50; 10-100; 0.05-50; 5-25; or 0.10-10—all these ranges being in mg lysozyme per kg feed (ppm).

For determining mg lysozyme protein per kg feed, the lysozyme is purified from the feed composition, and the specific activity of the purified lysozyme is determined using a relevant assay (see under lysozyme activity). The lysozyme activity of the feed composition as such is also determined using the same assay, and on the basis of these two determinations, the dosage in mg lysozyme protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg lysozyme protein in feed additives. Of course, if a sample is available of the lysozyme used for preparing the feed additive or the feed, the specific activity is determined from this sample (no need to purify the lysozyme from the feed composition or the additive).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", Nucl. Acids Res. (1 Jan. 2014) 42 (D1): D490-D495; see also www.cazy.org.

Thus the composition of the invention may also comprise at least one other enzyme selected from the group comprising of xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41), alpha-mannosidase (EC 3.2.1.24), mannanase (EC 3.2.1.25) and beta-glucanase (EC 3.2.1.4 or EC 3.2.1.6), or any combination thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Finase® and Quantum® Blue (AB Enzymes), OptiPhos® (Huvepharma) Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX and Ronozyme® G2 (DSM Nutritional Products), Econase® XT and Barley (AB Vista), Xylathin® (Verenium), Hostazym® X (Huvepharma) and Axtra® XB (Xylanase/beta-glucanase, DuPont).

In a particular embodiment, the composition of the invention comprises a protease (EC 3.4). Examples of commercially available proteases include Ronozyme® ProAct (DSM Nutritional Products).

Microbes

In an embodiment, the animal feed composition further comprises one or more additional microbes. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococcus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis*: 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29872, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day.

In another embodiment, the one or more bacterial strains are present in the form of a stable spore.

Premix

In an embodiment, the animal feed may include a premix, comprising e.g. vitamins, minerals, enzymes, amino acids, preservatives, antibiotics, other feed ingredients or any combination thereof which are mixed into the animal feed.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 2001/058275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs);

reactive oxygen generating species, anti-microbial peptides and anti-fungal polypeptides. Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of stabilizing agents (e.g. acidifiers) are organic acids. Examples of these are benzoic acid (VevoVitall®, DSM Nutritional Products), formic acid, butyric acid, fumaric acid and propionic acid.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid. Examples of amino acids which are used in animal feed are lysine, alanine, beta-alanine, threonine, methionine and tryptophan.

Use of Microbial Lyzozyme to Improve Animal Performance

In another aspect, the invention relates to the use of an animal feed additive or an animal feed for improving the European Production Efficiency Factor (EPEF) and/or Feed Conversion Ratio (FCR) in a monogastric animal wherein the animal feed or animal feed additive comprises one or more microbial lysozymes, wherein the microbial lysozyme is administered at a level of 8 to 250 ppm enzyme protein per kg animal feed.

In a preferred embodiment, the improvement is compared to an animal feed or animal feed additive wherein the microbial lysozyme is not present (herein referred to as the negative control).

In one embodiment, the EPEF is improved by at least 1%, such as by at least 1.5%, at least 2.0%, at least 2.5%, at least 3%, at least 3.5%, at least 4% or at least 5% compared to the control.

In another embodiment, the EPEF is improved by between 1% and 15%, such as between 1% and 12%, between 1% and 10%, 1.5% and 8%, 2.0% and 7% compared to the control, or any combination of these intervals.

In one embodiment, the FCR is improved by at least 1%, such as by at least 1.25%, at least 1.5%, at least 1.75% or at least 2.0% compared to the control. In another embodiment, the FCR is improved by between 1% and 5%, such as between 1% and 4%, between 1% and 3%, 1.25% and 2.5%, 1.5% and 2% compared to the control, or any combination of these intervals.

In one embodiment, the microbial lysozyme is dosed at a level of 9 to 200 ppm enzyme protein per kg animal feed, such as 10 to 150 ppm, 11 to 125 ppm, 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the monogastric animal is selected from the group consisting of swine, piglet, growing pig, sow, poultry, turkey, duck, quail, guinea fowl, goose, pigeon, squab, chicken, broiler, layer, pullet and chick, horse, crustaceans, shrimps, prawns, fish, amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish. In a preferred embodiment, the monogastric animal is selected from the group consisting of swine, piglet, growing pig, sow, poultry, turkey, duck, quail, guinea fowl, goose, pigeon, squab, chicken, broiler, layer, pullet and chick. In a more preferred embodiment, the monogastric animal is selected from the group consisting of swine, piglet, growing pig, sow, chicken, broiler, layer, pullet and chick.

In one embodiment, the microbial lysozyme has antimicrobial activity towards *Clostridium perfringens*. In an embodiment, the microbial lysozyme has at least 60%, at least 70%, at least 80%, at least 85%, at least 90%, at least 95% or at least 100% of the antimicrobial activity of SEQ ID NO: 1 against *Clostridium perfringens* under the conditions 50% MHB, pH 6. In an embodiment, the microbial lysozyme has at least 60%, at least 70%, at least 80%, at least 85%, at least 90%, at least 95% or at least 100% of the antimicrobial activity of SEQ ID NO: 4 against *Clostridium perfringens* under the conditions 50% MHB, pH 6. In an embodiment, the microbial lysozyme has at least 60%, at least 70%, at least 80%, at least 85%, at least 90%, at least 95% or at least 100% of the antimicrobial activity of SEQ ID NO: 12 against *Clostridium perfringens* under the conditions 50% MHB, pH 6. Antimicrobial activity towards *Clostridium perfringens* can be determined according to the antimicrobial assay described in Example 6.

In another embodiment, the invention relates to a composition comprising a microbial lysozyme for the treatment of *Clostridium perfringens* in a monogastric animal wherein the composition improves the European Production Efficiency Factor (EPEF) and/or feed conversion ratio (FCR) of the monogastric animal.

In one embodiment, the microbial lysozyme is fed to the animal from birth until slaughter. In a preferred embodiment the microbial lysozyme is fed to the animal on a daily basis from birth until slaughter. In another preferred embodiment the microbial lysozyme is fed to the animal on a daily basis for at least 10 days, such as at least 15 days or at least 20 days (where the days can be continuous or non-continuous) during the life span of the animal. In another embodiment, the microbial lysozyme is fed to the animal for 10-20 days followed by a non-treatment period of 5-10 days, and this cycle is repeated during the life span of the animal.

In a further embodiment, the microbial lysozyme is fed to broilers for the first 49 days after hatching. In a further embodiment, the microbial lysozyme is fed to broilers for the first 36 days after hatching. In a further embodiment, the microbial lysozyme is fed to broilers on days 22 to 36 after hatching. In a further embodiment, the microbial lysozyme is fed to broilers during the pre-starter (days 1-7) period. In a further embodiment, the microbial lysozyme is fed to broilers during the starter (days 8-22) period. In a further embodiment, the microbial lysozyme is fed to broilers during the pre-starter (days 1-7) and starter (days 8-22) period.

In a further embodiment, the microbial lysozyme is fed to layers during the life span of the animal. In a further embodiment, the microbial lysozyme is fed to layers for 76 weeks from hatching. In a further embodiment, the microbial lysozyme is fed to layers during the laying period, (from ca. week 18). In a further embodiment, the microbial lysozyme is fed to layers during the laying period but withheld during the forced molting period.

In a further embodiment, the microbial lysozyme is fed to turkeys during life span of the animal. In a further embodiment, the microbial lysozyme is fed to turkeys for 24 weeks from hatching. In a further embodiment, the microbial lysozyme is fed to turkeys for the first 16 weeks from hatching (for hens) and for the first 20 weeks for hatching (for toms).

In a further embodiment, the microbial lysozyme is fed to swine during life span of the animal. In a further embodiment, the microbial lysozyme is fed to swine for 27 weeks from birth. In a further embodiment, the microbial lysozyme is fed to piglets from birth to weaning (at 4 weeks). In a further embodiment, the microbial lysozyme is fed to piglets for the first 6 weeks from birth (4 weeks of lactation and 2 weeks post-weaning). In a further embodiment, the microbial lysozyme is fed to weaning piglets during the pre-starter (days 1-14 after weaning). In a further embodiment, the microbial lysozyme is fed to weaning piglets during the starter (days 15-42 after weaning) period. In a further embodiment, the microbial lysozyme is fed to weaning piglets during the pre-starter (days 1-14 after weaning) and starter (days 15-42 after weaning) period. In a further embodiment, the microbial lysozyme is fed to swine during the grower/fattening period (week 10 to ca. week 27 after birth).

In one embodiment, the microbial lysozyme is of fungal origin. In an embodiment, the microbial lysozyme is obtained or obtainable from the phylum Ascomycota, such as the sub-phylum Pezizomycotina.

In one embodiment, the microbial lysozyme comprises one or more domains selected from the list consisting of GH24 and GH25.

Methods of Altering the Population of Bacteria in the GI Tract of an Animal

In one aspect, the invention relates to a method of increasing the proportion of bacteria of genus *Faecalibacterium* in the microbiome of the GI tract of a monogastric animal comprising administering to the animal an animal feed or animal feed additive comprising one or more microbial lysozymes administered at a level of 8 to 250 ppm enzyme protein per kg animal feed.

In one embodiment, the proportion of bacteria of genus *Faecalibacterium* is increased by factor of at least 1.25, such as at least 1.50, at least 1.75, at least 2.0, at least 2.5 or at least 3.0.

In one embodiment, the proportion of bacteria of genus *Faecalibacterium* is increased by at least 1%, such as at least 2%, at least 3%, at least 4% or at least 5%.

In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the microbial lysozyme is fed to the animal using one of the regimes as disclosed herein.

In one embodiment, the microbial lysozyme is of fungal origin. In an embodiment, the microbial lysozyme is obtained or obtainable from the phylum Ascomycota, such as the sub-phylum Pezizomycotina.

In one embodiment, the microbial lysozyme comprises one or more domains selected from the list consisting of GH24 and GH25.

In one embodiment, the method increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by at least 1%, such as at least 2%, at least 3%, at least 4% or at least 5%. In an alternative embodiment, the proportion of bacteria of genus *Faecalibacterium* is increased by a factor of at least 1.25, such as at least 1.50, at least 1.75, at least 2.0, at least 2.5 or at least 3.0.

In one embodiment, the method improves the European Production Efficiency Factor (EPEF) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by at least 1%, such as at least 2%, at least 3%, at least 4% or at least 5% and the EPEF is increased by at least 1.25%, preferably by at least 1.5%, at least 1.75%, at least 2%, at least 3%, at least 4% or most preferably by at least 5%.

In one embodiment, the method improves the European Production Efficiency Factor (EPEF) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by factor of at least 1.25, such as at least 1.50, at least 1.75, at least 2.0, at least 2.5 or at least 3.0 and the EPEF is increased by at least 1.25%, preferably by at least 1.5%, at least 1.75%, at least 2%, at least 3%, at least 4% or most preferably by at least 5%.

In one embodiment, the method improves the Feed Conversion Ratio (FCR) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by at least 1%, such as at least 2%, at least 3%, at least 4% or at least 5% and the FCR is increased by at least 1.25%, preferably by at least 1.5% or most preferably by at least 1.75%.

In one embodiment, the method improves the Feed Conversion Ratio (FCR) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13. In an embodiment, the proportion of bacteria of genus *Faecalibacterium* is increased by factor of at least 1.25, such as at least 1.50, at least 1.75, at least 2.0, at least 2.5 or at least 3.0 and the FCR is increased by at least 1.25%, preferably by at least 1.5% or most preferably by at least 1.75%.

In one preferred embodiment, the invention relates to a method of increasing the proportion of bacteria of genus *Faecalibacterium* in the microbiome of the GI tract of a monogastric animal comprising administering to the animal an animal feed or animal feed additive comprising one or more microbial lysozymes administered at a level of 10 to 150 ppm enzyme protein per kg animal feed, wherein:

(a) the microbial lysozyme is a GH24 lysozyme obtained or obtainable from the phylum Ascomycota, preferably the sub-phylum Pezizomycotina;

(b) the monogastric animal is a selected from the group consisting of swine, piglet, growing pig, sow, chicken, broiler, layer, pullet and chick; and (c) the proportion of bacteria of genus *Faecalibacterium* in the microbiota of the GI tract of an animal is increased by at least 1%.

In one embodiment, the proportion of bacteria of genus *Faecalibacterium* is increased by at least 2%, such as at least 3%, at least 4% or at least 5%. In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals. In one embodiment, the microbial lysozyme is fed to the animal using one of the regimes as disclosed herein.

In one embodiment, the method further improves EPEF by at least 1%, such as by at least 1.5%, at least 2.0%, at least 2.5%, at least 3%, at least 3.5%, at least 4% or at least 5% compared to the control. In another embodiment, the method further improves EPEF by between 1% and 15%, such as between 1% and 12%, between 1% and 10%, 1.5% and 8%, 2.0% and 7% compared to the control, or any combination of these intervals.

In one embodiment, the method further improves FCR by at least 1%, such as by at least 1.25%, at least 1.5%, at least 1.75% or at least 2.0% compared to the control. In another embodiment, the method further improves FCR by between 1% and 5%, such as between 1% and 4%, between 1% and 3%, 1.25% and 2.5%, 1.5% and 2% compared to the control, or any combination of these intervals.

In one preferred embodiment, the invention relates to a method of increasing the proportion of bacteria of genus *Faecalibacterium* in the microbiome of the GI tract of a monogastric animal comprising administering to the animal an animal feed or animal feed additive comprising one or more microbial lysozymes administered at a level of 10 to 150 ppm enzyme protein per kg animal feed, wherein:

(a) the microbial lysozyme is a GH25 lysozyme obtained or obtainable from the phylum Ascomycota, preferably the sub-phylum Pezizomycotina;

(b) the monogastric animal is a selected from the group consisting of swine, piglet, growing pig, sow, chicken, broiler, layer, pullet and chick; and (c) the proportion of bacteria of genus *Faecalibacterium* in the microbiota of the GI tract of an animal is increased by at least 1%.

In one embodiment, the proportion of bacteria of genus *Faecalibacterium* is increased by at least 2%, such as at least 3%, at least 4% or at least 5%. In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals. In one embodiment, the microbial lysozyme is fed to the animal using one of the regimes as disclosed herein.

In one embodiment, the method further improves EPEF by at least 1%, such as by at least 1.5%, at least 2.0%, at least 2.5%, at least 3%, at least 3.5%, at least 4% or at least 5% compared to the control. In another embodiment, the method further improves EPEF by between 1% and 15%, such as between 1% and 12%, between 1% and 10%, 1.5% and 8%, 2.0% and 7% compared to the control, or any combination of these intervals.

In one embodiment, the method further improves FCR by at least 1%, such as by at least 1.25%, at least 1.5%, at least 1.75% or at least 2.0% compared to the control. In another embodiment, the method further improves FCR by between 1% and 5%, such as between 1% and 4%, between 1% and 3%, 1.25% and 2.5%, 1.5% and 2% compared to the control, or any combination of these intervals.

In one preferred embodiment, the invention relates to a method of increasing the proportion of bacteria of genus *Faecalibacterium* in the microbiome of the GI tract of a monogastric animal comprising administering to the animal an animal feed or animal feed additive comprising one or more microbial lysozymes administered at a level of 10 to 150 ppm enzyme protein per kg animal feed, wherein:

(a) the microbial lysozyme is a GH24 lysozyme obtained or obtainable from the phylum Ascomycota, preferably the sub-phylum Pezizomycotina;

(b) the monogastric animal is a selected from the group consisting of swine, piglet, growing pig, sow, chicken, broiler, layer, pullet and chick;

(c) the proportion of bacteria of genus *Faecalibacterium* in the microbiota of the GI tract of an animal is increased by at least 1%; and (d) the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13.

In one embodiment, the proportion of bacteria of genus *Faecalibacterium* is increased by at least 2%, such as at least 3%, at least 4% or at least 5%. In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals. In one embodiment, the microbial lysozyme is fed to the animal using one of the regimes as disclosed herein.

In one embodiment, the method further improves EPEF by at least 1%, such as by at least 1.5%, at least 2.0%, at least 2.5%, at least 3%, at least 3.5%, at least 4% or at least 5% compared to the control. In another embodiment, the method further improves EPEF by between 1% and 15%, such as between 1% and 12%, between 1% and 10%, 1.5% and 8%, 2.0% and 7% compared to the control, or any combination of these intervals.

In one embodiment, the method further improves FCR by at least 1%, such as by at least 1.25%, at least 1.5%, at least 1.75% or at least 2.0% compared to the control. In another embodiment, the method further improves FCR by between 1% and 5%, such as between 1% and 4%, between 1% and 3%, 1.25% and 2.5%, 1.5% and 2% compared to the control, or any combination of these intervals.

In one preferred embodiment, the invention relates to a method of increasing the proportion of bacteria of genus *Faecalibacterium* in the microbiome of the GI tract of a monogastric animal comprising administering to the animal an animal feed or animal feed additive comprising one or more microbial lysozymes administered at a level of 10 to 150 ppm enzyme protein per kg animal feed, wherein:

(a) the microbial lysozyme is a GH25 lysozyme obtained or obtainable from the phylum Ascomycota, preferably the sub-phylum Pezizomycotina;

(b) the monogastric animal is a selected from the group consisting of swine, piglet, growing pig, sow, chicken, broiler, layer, pullet and chick;

(c) the proportion of bacteria of genus *Faecalibacterium* in the microbiota of the GI tract of an animal is increased by at least 1%; and (d) the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 13.

In one embodiment, the proportion of bacteria of genus *Faecalibacterium* is increased by at least 2%, such as at least 3%, at least 4% or at least 5%. In one embodiment, the microbial lysozyme is dosed at a level of 11 to 125 ppm enzyme protein per kg animal feed, such as 12 to 100 ppm, 13 to 75 ppm, 15 to 50 ppm, 17.5 to 40 ppm, 25 to 75 ppm or 30 to 60 ppm enzyme protein per kg animal feed, or any combination of these intervals. In one embodiment, the microbial lysozyme is fed to the animal using one of the regimes as disclosed herein.

In one embodiment, the method further improves EPEF by at least 1%, such as by at least 1.5%, at least 2.0%, at least 2.5%, at least 3%, at least 3.5%, at least 4% or at least 5% compared to the control. In another embodiment, the method further improves EPEF by between 1% and 15%, such as between 1% and 12%, between 1% and 10%, 1.5% and 8%, 2.0% and 7% compared to the control, or any combination of these intervals.

In one embodiment, the method further improves FCR by at least 1%, such as by at least 1.25%, at least 1.5%, at least 1.75% or at least 2.0% compared to the control. In another embodiment, the method further improves FCR by between 1% and 5%, such as between 1% and 4%, between 1% and 3%, 1.25% and 2.5%, 1.5% and 2% compared to the control, or any combination of these intervals.

EXAMPLES

Strains

*Trichophaea saccata* CBS804.70 was purchased from the Centraalbureau voor Schimmelcultures (Utrecht, the Netherlands). According to Central Bureau vor Schnimmelkulture, *Trichophaea saccata* CBS804.70 was isolated from coal spoil tip soil from Staffordshire, England in May 1968.

According to Central Bureau vor Schnimmelkulture, *Acremonium alcalophilum* CBS 114.92 was isolated by A. Yoneda in 1984 from the sludge of pig faeces compost near Tsukui Lake, Japan.

Media and Solutions

YP+2% glucose medium was composed of 1% yeast extract, 2% peptone and 2% glucose.

YP+2% maltodextrin medium was composed of 1% yeast extract, 2% peptone and 2% maltodextrin.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, 10 g of sodium chloride, and deionized water to 1 liter.

COVE sucrose plates were composed of 342 g of sucrose, 20 g of agar powder, 20 ml of COVE salts solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, TRITON® X-100 (50 µl/500 ml) were added.

COVE salts solution was composed of 26 g of MgSO4.7H2O, 26 g of KCL, 26 g of KH2PO4, 50 ml of COVE trace metals solution, and deionized water to 1 liter.

COVE trace metals solution was composed of 0.04 g of Na2B4O7.10H2O, 0.4 g of CuSO4.5H2O, 1.2 g of FeSO4.7H2O, 0.7 g of MnSO4.H2O, 0.8 g of Na2MoO4.2H2O, 10 g of ZnSO4.7H2O, and deionized water to 1 liter.

Example 1: Cloning, Expression and Purification of the GH25 Lysozyme from *Acremonium alcalophilum* CBS 114.92

The GH25 lysozyme from *Acremonium alcalophilum* CBS 114.92 (SEQ ID NO: 1) was cloned and expressed as described in example 8 and purified as described in example 5 of WO 2013/076253. Alternatively, SEQ ID NO: 12 can be cloned and expressed as described in example 2 of WO 2013/076253.

Example 2: Expression of the GH24 Lysozyme from *Trichophaea saccata*

The fungal strain was cultivated in 100 ml of YP+2% glucose medium in 1000 ml Erlenmeyer shake flasks for 5 days at 20° C. Mycelia were harvested from the flasks by filtration of the medium through a Buchner vacuum funnel lined with MIRACLOTH® (EMD Millipore, Billerica, Mass., USA). Mycelia were frozen in liquid nitrogen and stored at −80° C. until further use. Genomic DNA was isolated using a DNEASY® Plant Maxi Kit (QIAGEN GMBH, Hilden Germany) according to the manufacturer's instructions.

Genomic sequence information was generated by Illumina MySeq (Illumina Inc., San Diego, Calif.). 5 μgs of the isolated *Trichophaea saccata* genomic DNA was used for library preparation and analysis according to the manufacturer's instructions. A 100 bp, paired end strategy was employed with a library insert size of 200-500 bp. One half of a HiSeq run was used for the total of 95,744,298, 100 bp raw reads obtained. The reads were subsequently fractionated to 25% followed by trimming (extracting longest subsequences having Phred-scores of 10 or more). These reads were assembled using Idba version 0.19. Contigs shorter than 400 bp were discarded, resulting in 8,954,791,030 bp with an N-50 of 10,035. Genes were called using GeneMark.hmm ES version 2.3c and identification of the catalytic domain was made using "Phage lysozyme PF00959" Hidden Markov Model provided by Pfam. The polypeptide coding sequence for the entire coding region was cloned from *Trichophaea saccata* CBS804.70 genomic DNA by PCR using the primers F-80470 and R-80470 (SEQ ID NO: 6 and SEQ ID NO: 7 respectively) as described below.

```
                                        (SEQ ID NO: 6)
5'-ACACAACTGGGGATCCACCATGCACGCTCTCACCCTTCT-3'
```

```
                                        (SEQ ID NO: 7)
5'-CTAGATCTCGAGAAGCTTTTAGCACTTGGGAGGGTGGG-3'
```

Bold letters represent *Trichophaea saccata* enzyme coding sequence. Restriction sites are underlined. The sequence to the left of the restriction sites is homologous to the insertion sites of pDau109 (WO 2005/042735).

Extensor HIFI PCR mix, 2× concentration (Thermo Scientific cat no AB-0795) was used for experiment.

The amplification reaction (25 μl) was performed according to the manufacturer's instructions (Thermo Scientific cat no AB-0795) with the following final concentrations:

PCR mix:
0.5 μM Primer F-80470
0.5 μM Primer R-80470
12.5 μl Extensor HIFI PCR mix, 2×conc.
11.0 μl H2O
10 ng of *Trichophaea saccata* CBS804.70 genomic DNA.

The PCR reaction was incubated in a DYAD® Dual-Block Thermal Cycler (BioRad, USA) programmed for 1 cycle at 94° C. for 30 seconds; 30 cycles each at 94° C. for 30 seconds, 52° C. for 30 seconds and 68° C. for 60 seconds followed by 1 cycle at 68° C. for 6 minutes. Samples were cooled to 10° C. before removal and further processing.

Three μl of the PCR reaction were analyzed by 1% agarose gel electrophoresis using 40 mM Tris base, 20 mM sodium acetate, 1 mM disodium EDTA (TAE) buffer. A major band of about 946 bp was observed. The remaining PCR reaction was purified directly with an ILLUSTRA™ GFX™ PCR DNA and Gel Band Purification Kit (GE Healthcare, Piscataway, N.J., USA) according to the manufacturer's instructions.

Two μg of plasmid pDau109 was digested with Bam HI and Hind III and the digested plasmid was run on a 1% agarose gel using 50 mM Tris base-50 mM boric acid-1 mM disodium EDTA (TBE) buffer in order to remove the stuffer fragment from the restricted plasmid. The bands were visualized by the addition of SYBR® Safe DNA gel stain (Life Technologies Corporation, Grand Island, N.Y., USA) and use of a 470 nm wavelength transilluminator. The band corresponding to the restricted plasmid was excised and purified using an ILLUSTRA™ GFX™ PCR DNA and Gel Band Purification Kit. The plasmid was eluted into 10 mM Tris pH 8.0 and its concentration adjusted to 20 ng per μl. An IN-FUSION® PCR Cloning Kit (Clontech Laboratories, Inc., Mountain View, Calif., USA) was used to clone the 983 bp PCR fragment into pDau109 digested with Bam HI and Hind III (20 ng). The IN-FUSION® total reaction volume was 10 μl. The IN-FUSION® total reaction volume was 10 μl. The IN-FUSION® reaction was transformed into FUSION-BLUE™ *E. coli* cells (Clontech Laboratories, Inc., Mountain View, Calif., USA) according to the manufacturer's protocol and plated onto LB agar plates supplemented with 50 μg of ampicillin per ml. After incubation overnight at 37° C., transformant colonies were observed growing under selection on the LB plates supplemented with 50 μg of ampicillin per ml.

Several colonies were selected for analysis by colony PCR using the pDau109 vector primers described below. Four colonies were transferred from the LB plates supplemented with 50 μg of ampicillin per ml with a yellow inoculation pin (Nunc A/S, Denmark) to new LB plates supplemented with 50 μg of ampicillin per ml and incubated overnight at 37° C.

```
Primer 8653:
                                        (SEQ ID NO: 8)
5'-GCAAGGGATGCCATGCTTGG-3'
```

```
Primer 8654:
                                        (SEQ ID NO: 9)
5'-CATATAACCAATTGCCCTC-3'
```

Each of the three colonies were transferred directly into 200 μl PCR tubes composed of 5 μl of 2× Extensor HIFI PCR mix, (Thermo Fisher Scientific, Rockford, Ill., USA), 0.5 μl of primer 8653 (10 pm/μl), 0.5 μl of primer 8654 (10 pm/μl), and 4 μl of deionized water. Each colony PCR was incubated in a DYAD® Dual-Block Thermal Cycler programmed for 1 cycle at 94° C. for 60 seconds; 30 cycles each at 95° C. for 30 seconds, 60° C. for 45 seconds, 72° C. for 60 seconds, 68° C. for 10 minutes, and 10° C. for 10 minutes.

Three μl of each completed PCR reaction were submitted to 1% agarose gel electrophoresis using TAE buffer. All four *E. coli* transformants showed a PCR band of about 980 bp. Plasmid DNA was isolated from each of the four colonies using a QIAprep Spin Miniprep Kit (QIAGEN GMBH, Hilden Germany). The resulting plasmid DNA was sequenced with primers 8653 and 8654 (SEQ ID NO: 8 and 9) using an Applied Biosystems Model 3730 Automated DNA Sequencer using version 3.1 BIG-DYE™ terminator chemistry (Applied Biosystems, Inc., Foster City, Calif., USA). One plasmid, designated pKKSC0312-2, was chosen for transforming *Aspergillus oryzae* MT3568. *A. oryzae* MT3568 is an amdS (acetamidase) disrupted gene derivative of *Aspergillus oryzae* JaL355 (WO 2002/40694) in which pyrG auxotrophy was restored by inactivating the *A. oryzae* amdS gene. Protoplasts of *A. oryzae* MT3568 were prepared according to the method described in European Patent, EP0238023, pages 14-15.

*E. coli* 3701 containing pKKSC0312-2 was grown overnight according to the manufacturer's instructions (Genomed) and plasmid DNA of pKKSC0312-2 was isolated using a Plasmid Midi Kit (Genomed JETquick kit, cat.nr. 400250, GENOMED GmbH, Germany) according to the manufacturer's instructions. The purified plasmid DNA was transformed into *Aspergillus oryzae* MT3568. *A. oryzae* MT3568 protoplasts were prepared according to the method of Christensen et al., 1988, Bio/Technology 6: 1419-1422. The selection plates consisted of COVE sucrose with +10 mM acetamide +15 mM CsCl+TRITON® X-100 (50 µl/500 ml). The plates were incubated at 37° C. Briefly, 8 µl of plasmid DNA representing 3 ugs of DNA was added to 100 µl MT3568 protoplasts. 250 µl of 60% PEG solution was added and the tubes were gently mixed and incubate at 37° for 30 minutes. The mix was added to 10 ml of pre melted Cove top agarose (The top agarose melted and then the temperature equilibrated to 40 C in a warm water bath before being added to the protoplast mixture). The combined mixture was then plated on two Cove-sucrose selection petri plates with 10 mM Acetamide. The plates were incubated at 37° C. for 4 days. Single *Aspergillus* transformed colonies were identified by growth on plates using the selection Acetimide as a carbon source. Each of the four *A. oryzae* transformants were inoculated into 750 µl of YP medium supplemented with 2% glucose and also 750 µl of 2% maltodextrin and also DAP4C in 96 well deep plates and incubated at 37° C. stationary for 4 days. At the same time the four transformants were restreaked on COVE-2 sucrose agar medium.

Culture broth from the *Aspergillus oryzae* transformants were then analyzed for production of the GH24 polypeptide by SDS-PAGE using NUPAGE® 10% Bis-Tris SDS gels (Invitrogen, Carlsbad, Calif., USA) according to the manufacturer's recommendations. A protein band at approximately 27 kDa was observed for each of the *Aspergillus oryzae* transformants. One *A. oryzae* transformant was cultivated in 1000 ml Erlenmeyer shake flasks containing 100 ml of DAP4C medium at 26° C. for 4 days with agitation at 85 rpm.

Example 3: Purification of the GH24 Lysozyme from *Trichophaea saccata*

The fermentation supernatant with the GH24 lysozyme from example 3 was filtered through a Fast PES Bottle top filter with a 0.22 µm cut-off. The resulting solution was diafiltrated with 5 mM Na-acetate, pH 4.5 and concentrated (volume reduced by a factor of 10) on an Ultra Filtration Unit (Sartorius) with a 10 kDa cut-off membrane.

After pretreatment about 275 mL of the lysozyme containing solution was purified by chromatography on SP Sepharose (approximately 60 mL) in a XK26 column eluting the bound lysozyme with 0 to 100% gradient of buffer A (50 mM Na-acetate pH 4.5) and buffer B (50 mM Na-acetate+1 M NaCl pH 4.5) over 10 column volumes. The fractions from the column were pooled based on the chromatogram (absorption at 280 and 254 nm) and SDS-PAGE analysis.

The molecular weight, as estimated from SDS-PAGE, was approximately 27 kDa and the purity was >90%.

Example 4: Other Characteristics for the GH24 Lysozyme from *Trichophaea saccata*

Determination of the N-terminal sequence was: YPVK-TDL.

The calculated molecular weight from this mature sequence is 26205.5 Da $(M+H)^+$.

The molecular weight determined by intact molecular weight analysis was 26205.3 Da. $(M+H)^+$.

The mature sequence (from EDMAN N-terminal sequencing data, intact molecular weight analysis and proteomic analysis):

```
                                          (SEQ ID NO: 4)
YPVKTDLHCRSSPSTSASIVRTYSSGTEVQIQCQTTGTSVQGSNVWDK

TQHGCYVADYYVKTGHSGIFTTKCGSSSGGGSCKPPPINAATVALIKE

FEGFVPKPAPDPIGLPTVGYGHLCKTKGCKEVPYSFPLTQETATKLLQ

SDIKTFTSCVSNYVKDSVKLNDNQYGALASWAFNVGCGNVQTSSLIKR

LNAGENPNTVAAQELPKWKYAGGKVMPGLVRRRNAEVALFKKPSSVQA

HPPKC.
```

Example 5: Determination of Lysozyme Activity

Lysozyme activity was determined by measuring the decrease (drop) in absorbance/optical density of a solution of resuspended *Micrococcus lysodeikticus* ATTC No. 4698 (Sigma-Aldrich M3770) or *Exiguobacterium undea* (DSM14481) measured in a spectrophotometer at 540 nm.
Preparation of *Micrococcus lysodeikticus* Substrate Before use the cells were resuspended in citric acid—phosphate buffer pH 6.5 to a concentration of 0.5 mg cells/mL and the optical density (OD) at 540 nm was measured. The cell suspension was then adjusted so that the cell concentration equalled an OD540=1.0. The adjusted cell suspension was then stored cold before use. Resuspended cells were used within 4 hours.
Preparation of Dried Cells of *Exiguobacterium undae* Substrate A culture of *E. undae* (DSM14481) was grown in 100 mL LB medium (Fluka 51208, 25 g/L) in a 500 mL shake-flask at 30° C., 250 rpm overnight. The overnight culture was then centrifuged at 20° C. and 5000 g for 10 minutes, and the pellet was then washed twice with sterile milliQ water, and resuspended in Milli-Q water. The washed cells were centrifuged for 1 minute at 13000 rpm and as much as possible of the supernatant was decanted. The washed cells were dried in a vacuum centrifuge for 1 hour. The cell pellet was resuspended in citric acid—phosphate buffer pH 4, 5 or 6 so that the optical density (OD) at 540 nm=1.
Measurement of Lysozyme Antimicrobial Activity in the Turbidity Assay The lysozyme sample to be measured was diluted to a concentration of 100-200 mg enzyme protein/L in citric acid—phosphate buffer pH 4, 5 or 6, and kept on ice until use. In a 96 well microtiterplate (Nunc) 200 µL of the substrate was added to each well, and the plate was incubated at 37° C. for 5 minutes in a VERSAmax microplate reader (Molecular Devices). Following incubation, the absorbance of each well was measured at 540 nm (start value). To start the activity measurement, 20 µL of the diluted lysozyme sample was added to each substrate (200 μL) and kinetic measurement of absorbance at 540 nm was initiated for minimum 30 minutes up to 24 hours at 37° C. The measured absorbance at 540 nm was monitored for each well and over time a drop in absorbance is seen if the lysozyme has lysozyme activity. The results are presented in table 2 below.

TABLE 2

Lysozyme Activity against *Micrococcus lysodeikticus* and *Exiguobacterium undea* as measured by Optical Density Drop

| Lysozyme | *Micrococcus lysodeikticus*[1] | *Exiguobacterium undae*[1] |
|---|---|---|
| GH22 lysozyme from *Gallus gallus* (SEQ ID NO: 5) | +++ (pH 6) | + (pH 6) |
| GH24 lysozyme from *Trichophaea saccate* (SEQ ID NO: 4) | ++ (pH 6) | ++ (pH 6) |
| GH25 lysozyme from *A. alcalophilum* (SEQ ID NO: 1) | + (pH 4) | + (pH 5) |

[1]– Means no effect; + means small effect; ++ means medium effect; +++ means large effect. The pH value in the brackets lists the assay pH based on lysozyme-substrate combination.

The data confirms that the GH22 lysozyme from *Gallus gallus*, the GH24 lysozyme from *Trichophaea saccata* and the GH25 lysozyme from *A. alcalophilum* all have lysozyme activity.

Example 6: Determination of Antimicrobial Activity

The antimicrobial activity of the GH25 lysozyme from *Aspergillus fumigatus* (SEQ ID NO: 1), the GH24 lysozyme from *Trichophaea saccata* (SEQ ID NO: 4) and the GH22 lysozyme from *Gallus gallus* (Hen Egg White lysozyme (HEWL), Sigma, 62971, SEQ ID NO: 5) against *Clostridium perfringens* DSM756 was tested using an RDA as described previously by Lehrer et al. (Lehrer R I, Rosenman M, Harwig S S et al. (1991), "Ultrasensitive assays for endogenous antimicrobial polypeptides", *J Immunol Methods,* 137:167-73), but with several modifications.

Briefly, RDA bacteria were prepared by streaking *C. perfringens* DSM756 from freeze stocks on Luria-Bertani agar plates (Sigma L3027) and the plates were incubated overnight at 37° C. under anaerobic conditions (Anaerogen, Oxoid) in a jar. The following day colonies were suspended in 0.9% NaCl and the suspensions were adjusted to McFarland std. 1. 87% sterile glycerol was added to give a final glycerol concentration of 20% and the cells were frozen at −80° C. until use. For estimation of colony forming units (CFU) per milliliter of the RDA bacteria 10-fold dilution series were prepared of the freeze stock in 0.9% NaCl and 100 μl of the dilutions were plated on Luria-Bertani agar plates (Sigma L3027) and incubated overnight at 37° C. under anaerobic conditions (Anaerogen, Oxoid) in a jar.

When preparing the RDA plates broth media with agar was melted and cooled to 42° C. Two media's were tested in the experiment:

a) ½ Mueller-Hinton broth (MHB) (Sigma/Fluka, 90922) (i.e. adjusted to pH6 with 4M HCl and diluted 1:1 with water) with 1.5% agarose, and b) ⅒ Mueller-Hinton broth (MHB) (Sigma/Fluka, 90922) (i.e. diluted 1:9 with water) with 1% agarose.

For each assay plate 30 ml of melted media was added to achieve around $5.0\times10^5$ cfu/mL *C. perfringens* DSM756 and this was poured into a single-well omnitray (Nunc) plate. The omnitray plate was overlaid with a TSP plate (Nunc) and left to solidify (at room temperature or below). Afterwards, the TSP plate was removed; leaving 96 wells, in which 10 μL of the compound of interest could be tested.

10 μl of the test solutions were spotted pr. well and the plates were incubated over night at 37° C. in a jar under anaerobic condition (Anaerogen, Oxoid). The following day a clearing zone indicated inhibition of growth of test bacteria and thereby antimicrobial activity. For the RDA plates with ½ MHB, the clearing zones were visualized by coloring with MTT (3-(4,5-dimethylthiazol-2-yl)-2,5-diphenyltetrazolium bromide, a yellow tertrazole), that is reduced to purple formazan in living cells (Mosmann, Tim (1983), "Rapid colorimetric assay for cellular growth and survival: application to proliferation and cytotoxicity assays", *Journal of Immunological Methods* 65 (1-2): 55-63). This coloring provides for a dark coloring of living cells and no coloring of the clearing zones without living cells.

Bacitracin zinc salt (Sigma B-8800) (50 μg/ml) was included as a positive control and lysozymes were tested using a solution of 100 μg/ml. The results are presented in table 3 below.

TABLE 3

Antimicrobial Activity against *Clostridium perfringens* as measure perfringensd by RDA

| | Diameter of clearing zone (mm) | | | |
|---|---|---|---|---|
| Experiment | 1 | 2 | 1 | 2 |
| Lysozyme | 1/10 MHB pH 7 | 1/10 MHB pH 7 | 1/2 MHB pH 6 | 1/2 MHB pH 6 |
| GH25 lysozyme from *A. alcalophilum* (SEQ ID NO: 1) | 13 | 11 | 6(20*) | 4(19*) |
| GH24 lysozyme from *Trichophaea saccata* (SEQ ID NO: 4) | 9 | 8 | 11 | 10 |
| GH22 lysozyme from *Gallus gallus* (SEQ ID NO: 5) | 11 | 9 | 0 | 0 |
| Bacitracin zinc salt | 23 | 20 | 13 | 11 |

*Incomplete inhibition of growth visible after MTT coloring

Both the GH24 lysozyme from *Trichophaea saccata* and the GH25 lysozyme from *Acremonium alcalophilum* showed antimicrobial activity against viable cells of *C. perfringens* DSM756 under both conditions tested. For the GH24 lysozyme from *Trichophaea saccata* zones of around 8-11 mm were present around the wells challenged with the enzyme. For the GH25 lysozyme from *Acremonium alcalophilum* a zone of 11-13 mm was present in ⅒ MBH, pH7, while in ½ MHB, pH 6 both a smaller clearing zone with a diameter of 4-6 mm and a larger incomplete clearing zone of 19-20 mm were present around the wells challenged with the enzyme. The larger incomplete clearing zone became present after coloring with MTT. For HEWL no zone of inhibition was observed in ½ MHB, pH 6, while in ⅒ MHB, pH7 growth inhibition was observed resulting in inhibition zones of 9-11 mm.

In conclusion, whilst HEWL only inhibitied growth in ⅒ MHB pH7, the GH24 lysozyme and the GH25 lysozyme surprisingly inhibitied growth of *C. perfringens* DSM756 under both sets of conditions.

Example 7: In Vivo Broiler Trial 1

Materials and Methods

The trial was performed at the Research Center for Animal Nutrition (DSM Nutritional Products France, F-68305 Village-Neuf) according to the official French guidelines for experiments with live animals. Day-old male broiler chickens ("ROSS PM3"), were supplied by a commercial hatchery (Joseph Grelier S. A., Elevage avicole de la Bohadière, F-49290 Saint-Laurent de la Plaine, France).

Animals and Housing

On the day of arrival (day 1), the chickens were divided by weight into groups of 20 birds. Each group was placed in one floor-pen littered with wood shavings and allocated to one of the different treatments.

Each treatment was replicated with 8 groups. The chickens were housed in an environmentally controlled room. The room temperature was adapted to the age of the birds. In the first few days an additional infra-red electric heating lamp was placed in each pen. Moreover, in the first week feed was offered to the birds as crumbled pellets, afterwards as pelleted feed. The birds had free access to feed and water.

Feeding and Treatments

The experimental diets (Starter and Grower) were based on soybean meal, wheat and rye (12%) as main ingredients (Table 4). The diets were formulated to contain 222 g crude protein and 12.5 MJ/kg $ME_N$ for the starter period and 204 g crude protein and 12.7 MJ/kg $ME_N$ for the grower period. The basal diets did not contain any coccidiostat.

TABLE 4

Composition and nutrient contents of the basal experimental diets

|  | Starter (d 1-22) | Grower (d 22-36) |
| --- | --- | --- |
| Ingredients (%) |  |  |
| Soybean meal | 37.65 | 32.80 |
| Corn | 22.35 | 23.05 |
| Wheat | 20.00 | 24.20 |
| Rye | 12.00 | 12.00 |
| Soya oil | 3.90 | 4.00 |
| DL-Methionine | 0.20 | 0.10 |
| L-Lysine | — | — |
| NaCl | 0.20 | 0.15 |
| DCP | 1.80 | 1.80 |
| CaCO3 | 0.90 | 0.90 |
| Premix[1] | 1.00 | 1.00 |
| Calculated content |  |  |
| Crude protein (%) | 22.2 | 20.4 |
| Metabolizable energy (MJ/kg)[2] | 12.5 | 12.6 |
| Analyzed content |  |  |
| Crude protein (%) | 22.4 | 20.1 |
| Metabolizable energy (MJ/kg)[3] | 12.8 | 12.7 |

[1]Vitamin-mineral premix provided per kilogram of diet: Vitamin A: 10'000 I.U.; vitamin E: 40 I.U.; vitamin K3: 3.0 mg; vitamin C: 100 mg; vitamin B1: 2.50 mg; vitamin B2: 8.00 mg; vitamin B6: 5.00 mg; vitamin B12: 0.03 mg; niacin: 50.0 mg; pantothenate calcium: 12.0 mg; folic acid: 1.50 mg; biotin 0.15 mg; cholin: 450 mg; ethoxyquine: 54 mg; Na: 1.17 g; Mg: 0.8 g; Mn: 80 mg; Fe: 60 mg; Cu: 30 mg; Zn: 54 mg; I: 1.24 mg; Co: 0.6 mg; Se: 0.3 mg
[1]Without coccidiostat;
[2]Calculated with EC-equation;
[3]Calculated with EC-equation based on analysed crude nutrients The diets were fed either unsupplemented (negative control, C), supplemented with the GH25 lysozyme (SEQ ID NO: 1) at 25, 50, 100, or 200 mg per kg feed or supplemented with Avilamycin at an inclusion level of 10 mg/kg as positive control. No additional enzymes (e.g. phytase) were added to the feed.

Appropriate amounts of the solid product (Avilamycin) was mixed with a small quantity of the basal feed as a premix which was then added to the feed to get the final concentration, according to the treatment. After mixing the feed was pelleted (3×25 mm) at about 70° C.

Appropriate amount of the liquid preparations of Lysozyme was diluted in water and sprayed onto the respective pelleted feed to get the final concentrations in the feed corresponding to the different treatments. For procedural balance of all treatments the same volume of water were also sprayed onto the pellets of the control diets Experimental Parameters and Analyses For the two experiments, the birds were weighed (as replicate group) on days 1, 22 and 36. The feed consumption for the intermediate periods was determined. Body weight gain and feed conversion ratio (feed/gain) were calculated.

The analyses of the nutrient content in the feed samples were performed according to standard methods (VDLUFA 1976). Nitrogen analysis was carried out with a Leco N analyzer (CP=N*6.25).

Statistical Analysis

For the statistical evaluation of performance data, a one-factorial analysis of variance (factor: treatment) was carried out. The software 'Stet Box Pro Agri', version 7.1.9 (Grimmer soft, 1985-2011) was used. Where significant treatment effects ($p<0.05$) were indicated, the differences among treatment means were subsequently determined with the Newman-Keuls test.

Results and Discussion

Based on the proximate chemical analyses in the diets the content of crude protein and metabolizable energy was close to the calculated content for both the starter and the grower diets (Table 4).

The results of the growth performance are summarized in table 5 for the two periods (starter period, day 1-22; grower period, day 22-36) and for the whole experimental period from day 1 to day 36.

During the starter period, although not significant, the supplementation of graded inclusion levels of microbial lysozyme was effective in improving the weight gain (WG), compared to the control diet. A numerical improvement by 1.3%, 2.4% and 4.2% was recorded with 25, 100 and 200 mg/kg of lysozyme, respectively. Moreover, the inclusion of 200 mg lysozyme resulted in comparable improvement of the WG as the inclusion of 10 mg/kg Avilamycin (+4.1%).

Lysozyme supplementation led to a significant improvement of the feed conversion ratio (FCR) compared to the control diet. The FCR was improved by 2.0%, 5.1% and 6.6% with the addition of 25, 100 and 200 mg/kg of lysozyme, respectively. The FCR was significantly different between the treatments supplemented with 25 and 200 mg/kg lysozyme. The inclusion of 100 and 200 mg/kg of lysozyme resulted in similar effect on FCR as the inclusion of 10 mg/kg Avilamycin.

The inclusion of the lysozyme at 25, 50 and 100 mg/kg led to a significant improvement of the FCR by 3.3%, 2.9% and 3.2%, respectively, compared to the control diet. The addition of Avilamycin resulted in a numerical improvement of the FCR by 2.3%, compared to the control diet. For the overall trial period from day 1 to day 36, lysozyme supplementation was not effective in improving the WG, although a positive trend (+1.6%) was recorded with the addition of 25 mg/kg lysozyme, compared to the control diet. A numerical improvement by 1.5% was recorded with the addition of 10 mg/kg Avilamycin. The feed intake was significantly affected with the addition of 100 mg/kg lysozyme compared to the control diet. However, the differences among the supplemented treatments were not significant.

The FCR was significantly improved with lysozyme and Avilamycin supplementation compared to the control diet. An improvement in a range of 2.1% to 4.4% was obtained with graded inclusion levels of lysozyme. Moreover, the inclusion of lysozyme at 100 mg/kg resulted in a significant better improvement of FCR compared to the inclusion of 200 mg/kg. Avilamycin supplementation led to a significant improvement by 4% compared to the control diet.

TABLE 5

Growth performance data[1] of male broiler chickens fed graded inclusion levels of microbial lysozyme

| | Product | | | | | | | | |
|---|---|---|---|---|---|---|---|---|---|
| | Starter (d 1-22) | | | Grower (d 22-36) | | | Whole period | | |
| Treatment | Weight gain (g/b) | Feed intake (g/b) | FCR | Weight gain (g/b) | Feed intake (g/b) | FCR | Weight gain (g/b) | Feed intake (g/b) | FCR |
| Control (C) | 1101 | 1995 | $1.816^a$ | 1760 | $3049^a$ | $1.734^{ab}$ | 2861 | $5047^a$ | $1.764^a$ |
| Avilamycin (10 mg/kg) | 1147 | 1943 | $1.695^c$ | 1757 | $2976^{ab}$ | $1.694^{abc}$ | 2903 | $4918^{ab}$ | $1.694^{bc}$ |
| Relative to C (%) | 104.1 | 97.4 | 93.3 | 99.8 | 97.6 | 97.7 | 101.5 | 97.5 | 96 |
| SEQ ID NO: 1 (25 mg/kg) | 1115 | 1985 | $1.781^{ab}$ | 1792 | $3004^{ab}$ | $1.676^c$ | 2908 | $4991^{ab}$ | $1.716^{bc}$ |
| Relative to C (%) | 101.3 | 99.5 | 98 | 101.9 | 98.5 | 96.7 | 101.6 | 98.9 | 97.3 |
| SEQ ID NO: 1 (50 mg/kg) | 1102 | 1977 | $1.793^{ab}$ | 1747 | $2939^{ab}$ | $1.683^{bc}$ | 2849 | $4920^{ab}$ | $1.727^b$ |
| Relative to C (%) | 100.1 | 99.1 | 98.7 | 99.3 | 96.4 | 97.1 | 99.6 | 97.5 | 97.9 |
| SEQ ID NO: 1 (100 mg/kg) | 1127 | 1941 | $1.723^{bc}$ | 1729 | $2870^b$ | $1.662^c$ | 2856 | $4815^b$ | $1.686^c$ |
| Relative to C (%) | 102.4 | 97.3 | 94.9 | 98.2 | 94.1 | 95.8 | 99.8 | 95.4 | 95.6 |
| SEQ ID NO: 1 (200 mg/kg) | 1148 | 1946 | $1.696^c$ | 1685 | $2934^{ab}$ | $1.742^a$ | 2832 | $4877^{ab}$ | $1.722^b$ |
| Relative to C (%) | 104.2 | 97.6 | 93.4 | 95.7 | 96.2 | 100.5 | 99 | 96.6 | 97.6 |
| P values | 0.269 | 0.603 | <0.001 | 0.065 | 0.028 | 0.001 | 0.273 | 0.017 | <0.001 |

Newman-Keuls test: Means within a row, not sharing a common superscript, are significantly different ($p < 0.05$).
[1]The performance were calculated with n = 8 groups of 20 birds per treatment.

Conclusion

The results obtained in the study showed that the inclusion of microbial lysozyme was effective in improving the feed conversion ratio of broilers fed diets formulated without coccidiostat and based on soybean meal, wheat and rye. Even at lower dosage (25 mg/kg) microbial lysozyme supplementation showed significant improvement of the FCR compared to the control diet. Moreover, the effects were comparable to these obtained with the inclusion of Avilamycin at 10 mg/kg.

Example 8: In Vivo Broiler Trial 2

The in vivo trial was carried out as described in example 7, except the feed was supplemented with the GH25 lysozyme (SEQ ID NO: 1) at 6.25, 12.5 or 25 mg per kg feed or supplemented with Avilamycin at an inclusion level of 10 mg/kg. No additional enzymes (e.g. phytase) were added to the feed.

The experimental diets (Starter and Grower) were based on soybean meal, wheat and rye (12%) as main ingredients (Table 6). The diets were formulated to contain 222 g crude protein and 12.5 MJ/kg $ME_N$ for the starter period and 204 g crude protein and 12.7 MJ/kg $ME_N$ for the grower period. The basal diets did not contain any coccidiostat.

TABLE 6

Composition and nutrient contents of the basal experimental diets

| | Starter (d 1-22) | Grower (d 22-36) |
|---|---|---|
| Ingredients (%) | | |
| Soybean meal | 34.70 | 30.00 |
| Corn | 25.45 | 25.55 |
| Wheat | 20.00 | 25.00 |
| Rye | 12.00 | 12.00 |
| Soya oil | 3.70 | 3.50 |
| DL-Methionine | 0.20 | 0.10 |
| L-Lysine | 0.05 | — |

TABLE 6-continued

Composition and nutrient contents of the basal experimental diets

| | Starter (d 1-22) | Grower (d 22-36) |
|---|---|---|
| NaCl | 0.20 | 0.15 |
| DCP | 1.80 | 1.80 |
| CaCO3 | 0.90 | 0.90 |
| Premix[1] | 1.00 | 1.00 |
| Calculated content | | |
| Crude protein (%) | 22.3 | 20.5 |
| Metabolizable energy (MJ/kg)[2] | 12.5 | 12.6 |
| Analyzed content | | |
| Crude protein (%) | 22.3 | 20.3 |
| Metabolizable energy (MJ/kg)[3] | 12.8 | 12.5 |

[1]Vitamin-mineral premix provided per kilogram of diet: Vitamin A: 10'000 I.U.; vitamin E: 40 I.U.; vitamin K3: 3.0 mg; vitamin C: 100 mg; vitamin B1: 2.50 mg; vitamin B2: 8.00 mg; vitamin B6: 5.00 mg; vitamin B12: 0.03 mg; niacin: 50.0 mg; pantothenate calcium: 12.0 mg; folic acid: 1.50 mg; biotin 0.15 mg; cholin: 450 mg; ethoxyquine: 54 mg; Na: 1.17 g; Mg: 0.8 g; Mn: 80 mg; Fe: 60 mg; Cu: 30 mg; Zn: 54 mg; I: 1.24 mg; Co: 0.6 mg; Se: 0.3 mg
[1]Without coccidiostat;
[2]Calculated with EC-equation;
[3]Calculated with EC-equation based on analysed crude nutrients Results and Discussion Based on the proximate chemical analyses in the diets the content of crude protein and metabolizable energy was close to the calculated content for both the starter and the grower diets (Table 6).

The results of the growth performance are summarized in table 7 for the two periods (starter period, day 1-22; grower period, day 22-36) and for the whole experimental period from day 1 to day 36.

During the starter period, the supplementation of the lysozyme was not effective in improving significantly the weight gain (WG), compared to the control diet (C). However, a numerical improvement by 3.6% was recorded with the supplementation of lysozyme at 6.25 mg/kg. The inclusion of 12.5 and 25 mg/kg of lysozyme resulted in significantly better effect on FCR than the inclusion of 10 mg/kg Avilamycin. The FCR was numerically improved by 2.9% and 3.4% with the addition of 12.5 and 25 mg/kg lysozyme compared to the control diet. No improvement of the WG and the FCR was obtained with Avilamycin supplementation.

In the grower period, the supplementation of the lysozyme was not effective in improving significantly the WG and the FCR, compared to the control diet. Only numerical improvement by 2.9 and 2.0% was recorded for the WG and the FCR, respectively, with the supplementation of lysozyme at 25 mg/kg compared to the control diet. During this period, Avilamycin supplementation resulted in numerical improvement of the WG by 1.2%, whereas a significant improvement of the FCR by 5.8%, was recorded compared to the control diet.

For the overall trial period from day 1 to day 36, supplementation of the lysozyme was effective in improving the WG, compared to C, at inclusion level of 25 mg/kg (+2.0%). The FCR was significantly improved with lysozyme (2.2%) at 25 mg/kg and Avilamycin (2.6%) supplementation compared to the control diet. Further, a numerical improvement in the FCR of 1.9% was obtained using lysozyme at 12.5 mg/kg.

ingredients (Table 8). The diets were formulated to contain 225 g crude protein and 12.5 MJ/kg $ME_N$ for the starter period, 215 g crude protein and 12.8 MJ/kg $ME_N$ for the grower period and 205 g crude protein and 13.0 MJ/kg $ME_N$ for the finisher period.

TABLE 8

Composition and nutrient contents of the basal experimental diets

|  | Starter (d 1-22) | Grower (d 22-36) | Finisher (d 36-42) |
| --- | --- | --- | --- |
| Ingredients (%) |  |  |  |
| Soybean meal | 38.00 | 35.40 | 33.00 |
| Corn | 22.55 | 20.20 | 21.40 |
| Wheat | 20.00 | 24.50 | 25.00 |
| Rye | 12.00 | 12.00 | 12.00 |
| Soya oil | 3.80 | 4.30 | 4.85 |

TABLE 7

Growth performance data[1] of male broiler chickens fed graded inclusion levels of microbial lysozyme

|  | Starter (d 1-22) | | | Grower (d 22-36) | | | Whole period | | |
| --- | --- | --- | --- | --- | --- | --- | --- | --- | --- |
| Treatment | Weight gain (g/b) | Feed intake (g/b) | FCR | Weight gain (g/b) | Feed intake (g/b) | FCR | Weight gain (g/b) | Feed intake (g/b) | FCR |
| Control (C) | 1067 | 1471[bcd] | 1.379[ab] | 1586 | 2730 | 1.721[a] | 2653 | 4188 | 1.578[ab] |
| Avilamycin (10 mg/kg) | 1070 | 1517[a] | 1.421[a] | 1605 | 2599 | 1.621[b] | 2675 | 4111 | 1.537[c] |
| Relative to C (%) | 100.2 | 103.1 | 103 | 101.2 | 95.2 | 94.2 | 100.8 | 98.1 | 97.4 |
| SEQ ID NO: 1 (6.25 mg/kg) | 1106 | 1551[ab] | 1.403[ab] | 1545 | 2705 | 1.753[a] | 2651 | 4249 | 1.604[a] |
| Relative to C (%) | 103.6 | 105.4 | 101.8 | 97.4 | 99.1 | 101.9 | 99.9 | 101.4 | 101.6 |
| SEQ ID NO: 1 (12.5 mg/kg) | 1049 | 1403[d] | 1.339[b] | 1581 | 2671 | 1.692[a] | 2630 | 4069 | 1.548[bc] |
| Relative to C (%) | 98.3 | 95.4 | 97.1 | 99.7 | 97.8 | 98.3 | 99.1 | 97.1 | 98.1 |
| SEQ ID NO: 1 (25 mg/kg) | 1076 | 1434[cd] | 1.332[b] | 1633 | 2753 | 1.686[a] | 2709 | 4181 | 1.543[c] |
| Relative to C (%) | 100.9 | 97.4 | 96.6 | 102.9 | 100.8 | 98 | 102.1 | 99.8 | 97.8 |
| P values | 0.205 | <0.001 | 0.002 | 0.303 | 0.131 | 0.001 | 0.69 | 0.231 | <0.001 |

Newman-Keuls test: Means within a row, not sharing a common superscript, are significantly different ($p < 0.05$).
[1]The performance were calculated with n = 8 groups of 20 birds per treatment.

Conclusion

The results obtained in the study showed that the inclusion of a microbial lysozyme was effective in improving the feed conversion ratio of broilers fed diets formulated without coccidiostat and based on soybean meal, wheat and rye. At 25 mg/kg, the microbial lysozyme supplementation showed significant improvement of the FCR compared to the control diet and even at 12.5 mg/kg, the microbial lysozyme showed numeral improvements. Moreover, the effects were comparable to these obtained with the inclusion of Avilamycin at 10 mg/kg.

Example 9: In Vivo Broiler Trial 3

The in vivo trial was carried out as described in example 7, except the feed was supplemented with the GH25 lysozyme (SEQ ID NO: 1) at 12.5 or 25 mg per kg feed, the GH24 lysozyme (SEQ ID NO: 4) at 12.5 or 25 mg per kg feed or with Avilamycin at an inclusion level of 10 mg/kg. No additional enzymes (e.g. phytase) were added to the feed.

The experimental diets (Starter, Grower and Finisher) were based on soybean meal, wheat and rye (12%) as main TABLE 8-continued Composition and nutrient contents of the basal experimental diets

|  | Starter (d 1-22) | Grower (d 22-36) | Finisher (d 36-42) |
| --- | --- | --- | --- |
| DL-Methionine | 0.20 | 0.15 | 0.15 |
| NaCl | 0.15 | 0.15 | 0.15 |
| DCP | 1.70 | 1.85 | 1.95 |
| CaCO3 | 0.54 | 0.39 | 0.34 |
| Premix[1] | 1.00 | 1.00 | 1.00 |
| Coccidiostat | 0.06 | — | — |
| Calculated content |  |  |  |
| Crude protein (%) | 22.5 | 21.5 | 20.5 |
| Metabolizable energy (MJ/kg)[2] | 12.6 | 12.8 | 13.0 |

TABLE 8-continued

Composition and nutrient contents of the basal experimental diets

| | Starter (d 1-22) | Grower (d 22-36) | Finisher (d 36-42) |
|---|---|---|---|
| Analyzed content | | | |
| Crude protein (%) | 21.9 | 21.5 | 20.8 |
| Metabolizable energy (MJ/kg)[3] | 12.5 | 12.6 | 12.9 |

[1]Vitamin-mineral premix provided per kilogram of diet: Vitamin A: 10'000 I.U.; vitamin E: 40 I.U.; vitamin K3: 3.0 mg; vitamin C: 100 mg; vitamin B1: 2.50 mg; vitamin B2: 8.00 mg; vitamin B6: 5.00 mg; vitamin B12: 0.03 mg; niacin: 50.0 mg; pantothenate calcium: 12.0 mg; folic acid: 1.50 mg; biotin 0.15 mg; cholin: 450 mg; ethoxyquine: 54 mg; Na: 1.17 g; Mg: 0.8 g; Mn: 80 mg; Fe: 60 mg; Cu: 30 mg; Zn: 54 mg; I: 1.24 mg; Co: 0.6 mg; Se: 0.3 mg.
[1]Without coccidiostat;
[2]Calculated with EC-equation;
[3]Calculated with EC-equation based on analysed crude nutrients.

Results and Discussion

Based on the analyzed chemical compositions of the diets, the content of crude protein was close to the calculated content but the metabolizable energy was higher than expected in all the three diets (starter-grower and finisher) (Table 8).

The results of the growth performance are summarized in table 9 for the two periods (starter period, day 1-22; grower period, day 22-36, finisher period, day 36-42) and for the whole experimental period from day 1 to day 42 (table 10).

TABLE 9

Growth performance data of male broiler chickens fed graded inclusion levels of microbial lysozyme

| | Starter (d 1-22) | | | Grower (d 22-36) | | | Finisher (d 36-42) | | |
|---|---|---|---|---|---|---|---|---|---|
| Treatment | Weight gain (g/b) | Feed intake (g/b) | FCR | Weight gain (g/b) | Feed intake (g/b) | FCR | Weight gain (g/b) | Feed intake (g/b) | FCR |
| Control (C) | 1096 | 1578 | 1.440 | 1328 | 2285 | 1.723 | 761 | 1487 | 1.960 |
| Avilamycin (10 mg/kg) | 1102 | 1593 | 1.452 | 1334 | 2242 | 1.683 | 738 | 1460 | 1.982 |
| Relative to C (%) | 100.6 | 101.0 | 100.8 | 100.4 | 98.1 | 97.7 | 97.0 | 98.2 | 101.1 |
| SEQ ID NO: 1 (12.5 mg/kg) | 1106 | 1621 | 1.466 | 1365 | 2365 | 1.734 | 794 | 1544 | 1.953 |
| Relative to C (%) | 100.9 | 102.7 | 101.8 | 102.8 | 103.5 | 100.6 | 104.2 | 103.8 | 99.6 |
| SEQ ID NO: 1 (25 mg/kg) | 1129 | 1596 | 1.413 | 1364 | 2308 | 1.692 | 775 | 1522 | 1.968 |
| Relative to C (%) | 103.0 | 101.1 | 98.1 | 102.7 | 101.0 | 98.2 | 101.8 | 102.3 | 100.4 |
| SEQ ID NO: 4 (12.5 mg/kg) | 1095 | 1608 | 1.469 | 1359 | 2298 | 1.692 | 795 | 1560 | 1.969 |
| Relative to C (%) | 99.9 | 101.9 | 102.0 | 102.4 | 100.5 | 98.2 | 104.4 | 104.8 | 100.4 |
| SEQ ID NO: 4 (25 mg/kg) | 1133 | 1603 | 1.414 | 1364 | 2336 | 1.714 | 800 | 1524 | 1.919 |
| Relative to C (%) | 103.4 | 101.6 | 98.1 | 102.7 | 102.2 | 99.5 | 105.1 | 102.5 | 97.9 |

TABLE 10

Growth performance summary of male broiler chickens fed graded inclusion levels of microbial lysozyme

| | Whole period | | | | |
|---|---|---|---|---|---|
| Treatment/ Product | Weight gain (g/b) | Feed intake (g/b) | FCR | Motality | EPEF |
| Control (C) | 3186 | 5351 | 1.680 | 7.5 | 418 |
| Avilamycin (10 mg/kg) | 3184 | 5312 | 1.669 | 12.5 | 397 |
| Relative to C (%) | 99.9 | 99.3 | 99.3 | | 95.0 |
| SEQ ID NO: 1 (12.5 mg/kg) | 3264 | 5529 | 1.695 | 13.1 | 398 |
| Relative to C (%) | 102.5 | 103.3 | 100.9 | | 95.2 |
| SEQ ID NO: 1 (25 mg/kg) | 3269 | 5426 | 1.660 | 8.8 | 428 |
| Relative to C (%) | 102.6 | 101.4 | 98.8 | | 102.4 |
| SEQ ID NO: 4 (12.5 mg/kg) | 3249 | 5466 | 1.683 | 11.3 | 408 |
| Relative to C (%) | 102.0 | 102.1 | 100.2 | | 97.6 |
| SEQ ID NO: 4 (25 mg/kg) | 3290 | 5450 | 1.657 | 10.0 | 425 |
| Relative to C (%) | 103.3 | 101.9 | 98.6 | | 101.7 |

Over the whole period, the GH24 and GH25 lysozyme supplemented at 25 mg/kg resulted in FCR improvements of 1.2% and 1.4% respectively compared to NC diet. Furthermore, the GH24 and GH25 lysozyme supplemented at 25 mg/kg resulted in EPEF improvements of 2.4% and 1.7% respectively compared to NC diet. Whilst the positive control Avilamycin showed a slight FCR improvement of 0.7%, the EPEF was worse by 5.0%. In this trial, the lower supplement of 12.5 mg/kg of the GH24 and GH25 lysozyme did not show any benefit over the NC diet.

Conclusion

The results obtained in the study showed that the inclusion of a microbial lysozyme at 25 mg/kg was effective in improving the FCR and the EPEF of broilers fed diets formulated with coccidiostat in the starter period and based on soybean meal, corn, wheat and rye. In addition, the microbial lysozyme at 25 mg/kg was markedly better in improving the EPEF over the positive control (Avilamycin).

Example 10: In Vivo Piglet Trial

Materials and Methods

The trial was performed from Oct. 23 to Dec. 4, 2014 at the Research Center for Animal Nutrition (DSM Nutritional Products France, F-68305 Village-Neuf) according to the official French guidelines for experiments with live animals.

Animals and Housing

One hundred and four castrated male crossbred (Large-White (female)×Redon (male)) weaned piglets having 28 days of age supplied by the commercial farm "Elevage de la Plaine du Rhin" located in Balgau (France), were used in a 42-day experiment. The initial bodyweight of the piglets was 7.88±0.675 kg. They were sorted by body weight into 32 groups of 3 or 4 piglets and randomly allotted to each dietary treatment. Each group of animals was placed in one flat-deck cages and allocated to one of the different treatments.

Each treatment was replicated with 8 cages using a total of 26 animals (6 cages of 3 animals/treatment and 2 cages of 4 animals/treatment) per treatment. Each cage had a plastic-coated welded wire floor and was equipped with two water nipples and two stainless-steel individualised feeders. Animals were housed in an environmentally controlled room. Room temperature was initially 27° C. and was lowered weekly by about 2° C. until 21-22° C. and relative humidity percentage was 50%.

Feeding and Treatments

The experimental diets (Pre-Starter and Starter) were fed ad libitum in two feeding phases from day 0 to 14 (phase 1, Pre-starter) and day 14 to 42 (phase 2, Starter). The ingredient composition and the calculated nutrient levels of the experimental diets for phases 1 and 2 are presented in table 11. The analysed content is presented in table 12. Both diets were formulated to meet the animals' requirements according NRC (2012) and were fed in pelleted form. Pelleting conditions were at 70° C. for 30 seconds.

TABLE 11

Composition and nutrient contents of the basal experimental diets

|  | Pre-starter (%) | Starter (%) |
|---|---|---|
| Ingredients | | |
| Barley | 38.00 | 38.00 |
| Wheat | 22.10 | 17.50 |
| Soybean meal 48% | 24.00 | 22.00 |
| Maize | 6.00 | 16.20 |
| Soybean oil | 1.00 | 2.00 |
| Dried whey | 5.00 | — |
| Vermiculite | — | 1.00 |
| Calcium carbonate | 0.30 | 0.30 |
| L-Lysine HCl | 0.10 | — |
| Vitamin-mineral Premix 3136[1] | 3.50 | 3.00 |
| Estimated nutrient content | | |
| Crude protein (%) | 19.47 | 17.95 |
| Lysine (%) | 1.24 | 1.03 |
| Threonine (%) | 0.67 | 0.61 |
| Methionine + cysteine (%) | 0.70 | 0.66 |
| Total P (%) | 0.71 | 0.64 |
| Total Ca (%) | 0.84 | 0.71 |
| Estimated digestible energy (MJ/kg) | 13.62 | 13.87 |

[1]Vitamin-mineral premix 3136 provided per kilogram of diet: Vitamin A: 20'000 I.U.; Vitamin E: 100 mg.; Vitamin K: 4.0 mg; Vitamin C: 200 mg; Vitamin B1: 5.00 mg; Vitamin B2: 10.00 mg; Vitamin B6: 8.00 mg; Vitamin B12: 0.07 mg; Niacin: 60.0 mg; Pantothenic acid: 40.0 mg; Folic acid: 3.00 mg; Biotin 0.4 mg; Choline: 800 mg; Mn: 60.5 mg; Fe: 162 mg; Cu: 9.5 mg; Zn: 100 mg; I: 0.9 mg; Se: 0.3 mg

TABLE 12

Analysed nutrient contents of the basal diets

| Analyzed nutrient content | Pre-starter | Starter |
|---|---|---|
| Dry matter (%) | 87.89 | 87.42 |
| Crude protein (% DM) | 21.69 | 19.63 |
| Crude Ash (% DM) | 6.41 | 6.37 |
| Fat (% DM) | 4.15 | 5.42 |
| Starch (% DM) | 44.63 | 49.54 |
| Total P (mg/g DM) | 8.24 | 7.50 |
| Total Ca (mg/g DM) | 9.01 | 7.69 |
| Total Zn (mg/g DM) | 0.28 | 0.25 |
| Gross energy (MJ/kg DM) | 18.42 | 18.67 |

The diets were fed either unsupplemented (negative control) or supplemented with the GH25 lysozyme (SEQ ID NO: 1) at 50 mg per kg feed, the GH24 lysozyme (SEQ ID NO: 4) at 50 mg per kg feed or VevoVital at 5000 mg per kg feed. No additional enzymes (e.g. phytase) were added to the feed.

| Treatment | Product | Inclusion level (mg/kg) |
|---|---|---|
| A | Negative control | — |
| B | VevoVital | 5000 |
| C | SEQ ID NO: 1 | 50 |
| D | SEQ ID NO: 4 | 50 |

VevoVital was mixed to the premixed mash diet before pelleting the diet.

Appropriate amount of the liquid preparations of lysozyme was diluted in water and sprayed onto the respective pelleted feed to get the final concentrations in the feed corresponding to the different treatments. For procedural balance of all treatments the same volume of water were also sprayed onto the pellets of the control diets.

Experimental Parameters and Analyses

The health status of the animals was controlled daily.

Body weight of the individual animals and feed consumption per pen were recorded on days 14 and 42 of the study. Performance, average daily weight gain (ADWG), average daily feed intake (ADFI) and feed conversion ratio (FCR) was calculated for phases 1 and 2, and the whole experimental period.

Statistical Analysis

The experimental unit was the piglet, except for ADFI and FCR which were measured by cage, and in both cases, treatment was used as class variable.

Statistical analyses were performed using the StatGraphics Centurion XVI statistical software package (Manugistics, Rockville, Md.).

One-factorial ANOVA and Student-Newman-Keuls test was used to assess differences among means in treatment groups.

Variability in the data was expressed as the pooled standard error. In all instances, differences were reported as significant at $P<0.05$.

Results and Discussion

Based on the analyzed chemical compositions of the diets, the content of crude protein (19.07% and 17.16% as is, in pre-starter and starter periods, respectively) was close to the calculated content (19.47% and 17.95% as is, in pre-starter and starter periods, respectively) (Table 12).

All piglets remained healthy throughout the study. During the enzyme supplementation, none of the animals showed any symptoms of illness or toxicosis due to the test compounds. Mortality rate was zero.

Results of the growth performance are summarized for the two periods (pre-starter period, day 0-14, and starter period, day 14-42) and for the whole experimental periods from day 0 to day 42 (Table 12). In general, excellent animal growth performance was obtained for all treatments.

No significant difference among the supplemented treatments was recorded in terms of body weight. However, the supplementation of either the GH25 lysozyme (SEQ ID NO: 1) or the GH24 lysozyme (SEQ ID NO: 4) at 50 mg/kg resulted in a numerical improvement of the ADWG by 4.0 and 11.8%, respectively during the starter period, and 2.4% and 7.8%, respectively during the whole period, compared to the negative control diet.

Over the pre-starter, starter and whole periods the supplementation of VevoVital resulted in an improvement of ADWG by 4.8, 5.8 and 5.4% compared to NC.

The results of FCR showed a statistically significant effect (p<0.05) of treatment in the pre-starter, starter and overall periods. Over the starter period, from day 15 to day 42, piglets, which received VevoVital (PC), the GH25 lysozyme (SEQ ID NO: 1) or the GH24 lysozyme (SEQ ID NO: 4) included at 50 mg/kg showed an improvement to FCR by 9.5, 11.3 and 9.1% compared to NC.

As presented in Table 13, during the overall period (day 0 to day 42) piglets receiving feed added with VevoVital (PC) at 5000 mg/kg, the GH25 lysozyme (SEQ ID NO: 1) or the GH24 lysozyme (SEQ ID NO: 4) (both enzymes added at 50 mg/kg) showed an improvement on FCR by 9.6, 9.6 and 7.1% respectively compared to the negative control.

No significant difference among the supplemented treatments was recorded in terms of EPEF. However, the supplementation of either the GH25 lysozyme (SEQ ID NO: 1) or the GH24 lysozyme (SEQ ID NO: 4) at 50 mg/kg resulted in a large numerical EPEF improvement by 13.0 and 15.3%, respectively during the whole period, compared to the negative control.

Conclusion

It can be concluded that in the present study and at the tested dosages and conditions, both lysozyme candidates supplemented at 50 mg per kg feed to soybean meal, maize, wheat and barley based diet had a numerically improvement on growth performance of piglets although this effect was not statistically significant. Improvement of BWG with the GH24 lysozyme (SEQ ID NO: 4) at 50 mg/kg feed was even higher than the positive control and there was a very large improvement of 13-15% in EPEF. Importantly, the results show a statistically significant effect of both GH25 lysozyme (SEQ ID NO: 1) and GH24 lysozyme (SEQ ID NO: 4) included at 50 mg/kg feed treatment on ADFI and FCR in the starter and overall periods.

Example 11: In Vivo Broiler Trial 4

Treatments and Diet Composition

The basal diet was based upon wheat, rye, soybean meal, fish meal and sunflower meal, and was formulated and adjusted in two phases (Starter and Grower periods of 7 and 17 days, respectively) according to the growing animals changing requirements. Diet composition was designed to meet or exceed the requirements except for metabolisable energy, phosphorus and calcium (tables 15 and 16).

Starter feed did not contain lysozyme but served for a similar rearing period of 7 days and introduction of the birds to the main diet components in the Grower feeds. During the Grower period, the lysozyme (SEQ ID NO: 1) was applied at 50 g/t as a liquid formulation (table 14). There were no other enzymes or any coccidiostats supplemented in the diets. The diets were prepared at a feedmill specialised in experimental diets and the mash feed was offered ad libitum to the birds.

TABLE 13

Growth performance data of piglets fed graded inclusion levels of microbial lysozyme

| | | day 0-14 | | | day 14-42 | | | day 0-42 | | | |
|---|---|---|---|---|---|---|---|---|---|---|---|
| Treatment | | ADFI (g/d)[2] | ADWG (g/d)[1] | FCR[2] | ADFI (g/d)[2] | ADWG (g/d)[1] | FCR[2] | ADFI (g/d)[2] | ADWG (g/d)[1] | FCR[2] | EPEF |
| Negative control (NC) | Mean | 360 | 290 | 1.240$^{ab}$ | 930$^{bc}$ | 603 | 1.544$^b$ | 734$^b$ | 499 | 1.484$^b$ | 339 |
| | SD | 20 | 66 | 0.053 | 34 | 79 | 0.096 | 23 | 69 | 0.072 | 24 |
| | % | 100 | 100 | 100 | 100 | 100 | 100 | 100 | 100 | 100 | 100 |
| VevoVital (PC) | Mean | 355 | 304 | 1.168$^a$ | 886$^{ab}$ | 638 | 1.398$^a$ | 709$^{ab}$ | 526 | 1.342$^a$ | 394 |
| | SD | 26 | 56 | 0.041 | 33 | 62 | 0.103 | 30 | 52 | 0.079 | 30 |
| | % relative NC | 98.6 | 104.8 | 94.2 | 95.3 | 105.8 | 90.5 | 96.6 | 105.4 | 90.4 | 116.2 |
| NC+ SEQ ID NO: 1 (50 ppm) | Mean | 324 | 279 | 1.170$^a$ | 862$^a$ | 627 | 1.379$^a$ | 683$^a$ | 511 | 1.341$^a$ | 383 |
| | SD | 51 | 84 | 0.085 | 38 | 84 | 0.076 | 37 | 78 | 0.070 | 52 |
| | % relative NC | 90.0 | 96.2 | 94.4 | 92.7 | 104.0 | 89.3 | 93.1 | 102.4 | 90.4 | 113.0 |
| NC+ SEQ ID NO: 4 (50 ppm) | Mean | 333 | 265 | 1.272$^b$ | 944$^c$ | 674 | 1.404$^a$ | 740$^b$ | 538 | 1.379$^a$ | 391 |
| | SD | 42 | 53 | 0.049 | 62 | 89 | 0.044 | 49 | 69 | 0.040 | 43 |
| | % relative NC | 92.5 | 91.4 | 102.6 | 101.5 | 111.8 | 90.9 | 100.8 | 107.8 | 92.9 | 115.3 |
| | P value | 0.317 | 0.346 | 0.014 | 0.013 | 0.068 | 0.009 | 0.034 | 0.341 | 0.004 | 0.068 |

[1]Mean ± mean deviation of 18 determinations;
[2]Mean ± mean deviation of 6 determinations;
[a,b,c]Different superscripts in the same column indicate a significant difference (p < 0.05);
ADFI: average daily feed intake;
ADWG: average daily weight gain.

TABLE 14

Study design

| Treatment | Lysozyme | Inclusion level (mg/kg) | Pens | Birds per pen |
|---|---|---|---|---|
| 1 | — | — | 16 | 40 |
| 2 | SEQ ID NO: 1 | 50 | 16 | 40 |

TABLE 15

Diet composition (g/kg)

| Phase | Starter (Days 1-7) | Grower (Days 8-24) |
|---|---|---|
| Wheat | 511.25 | 473.90 |
| Rye | 50.00 | 100.00 |
| Soybean Meal (48% XP) | 261.00 | 207.00 |
| Soybean Hulls[1] | 29.00 | 23.00 |
| Fishmeal 70% XP | 50.00 | 20.00 |
| Sunflower Meal (low XP) | | 70.00 |
| Animal Fat (Lard) | | 30.00 |
| Soybean Oil | 62.50 | 42.00 |
| Premix | 5.00 | 5.00 |
| Lime fine | 13.50 | 13.50 |
| Monocalciumphosphate | 9.50 | 4.80 |
| Salt | 1.20 | 1.30 |
| NaHCO3 | 2.10 | 2.60 |
| L-Lysine HCl | 1.35 | 2.70 |
| DL-Methionine | 2.60 | 2.60 |
| L-Threonine | 0.95 | 1.15 |
| L-Valine | 0.05 | 0.45 |

[1]Soybean hulls were introduced to the diet in order to simulate low protein SBM, which was not available as a single ingredient

TABLE 16

Premix composition

| Nutrient premix | Supplied per kg feed | Provided as |
|---|---|---|
| Vitamin A (retinyl acetate) | 12,000 IE | |
| Vitamin $D_3$ (cholecalciferol) | 2,400 IE | |
| Vitamin E (dl-a-tocopherol) | 50 mg | |
| Vitamin $K_3$ (menadione) | 1.5 mg | |
| Vitamin $B_1$ (thiamin) | 2.0 mg | |
| Vitamin $B_2$ (riboflavin) | 7.5 mg | |
| Vitamin $B_6$ (pyridoxine-HCl) | 3.5 mg | |
| Vitamin $B_{12}$ (cyanocobalamin) | 20 µg | |
| Niacin | 35 mg | |
| D-pantothenic acid | 10 mg | |
| Choline chloride | 460 mg | |
| Folic acid | 1.0 mg | |
| Biotin | 0.2 mg | |
| Iron | 80 mg | (267 mg $FeSO_4 \cdot H_2O$) |
| Copper | 12 mg | (48 mg $CuSO_4 \cdot 5H_2O$) |
| Manganese | 85 mg | (142 mg MnO) |
| Zinc | 60 mg | (169 mg $ZnSO_4 \cdot H_2O$) |
| Cobalt | 0.40 mg | (1.9 mg $CoSO_4 \cdot 7H_2O$) |
| Iodine | 0.8 mg | (1.1 mg KJ) |
| Selenium | 0.1 mg | (0.22 mg $Na_2SeO_3$) |
| Anti-oxidant mixture | 125 mg | Oxytrap PXN |

Animals and Housing

At the day of hatching, male day-old broiler type chickens (male byproducts of female parental line of Cobb 500) were obtained from Cobb Germany Avimex GmbH, Wiesenena (Brösenweg 80, 04509 Wiesenena).

The birds were randomly assigned in groups of 22 chickens to the experimental pens (~3 sq·m.) equipped with a bell drinker and a round feeder. After 7 days of equal rearing, number of birds per pen was reduced to 20, selecting against obviously light birds. Recorded body weights (BW) were immediately statistically evaluated. In order to ensure similar average BW between treatments and variation within treatments statistical evaluation of BW-placement of chicks was coordinated in such a way as to minimize within-pen variation and between-treatment differences of average BW.

Feed and water were freely available, feed consumption was recorded. Initial bedding consisted of wood shavings. Caked excreta patches around the drinkers were removed several times during the experimental period and more bedding material was added when required. Light and temperature regimes were managed according to the breeder's recommendations.

Birds were routinely vaccinated against Newcastle disease and Gumboro on day 18.

Data Recording and Calculation of Performance Parameters

Birds were weighed (groupwise) at placement and at the end of each fattening period. At the final weighing, birds were weighed individually. Feed offered was recorded continuously upon refilling the feeders; the feed remaining in the feeders was recorded at the end of each fattening period. From these data, feed consumption was calculated.

The weight of losses and culls was recorded upon occurrence.

Daily BW gain per bird (BW gain) and feed conversion ratio (FCR) were calculated as follows:

BWgain: difference between BW per bird at the end and at the beginning of the study divided by the number of days FCR: total feed consumption of a pen divided by total BW gain of that pen (total BW gain=total BW at the end+weight of removals and losses−total BW at the beginning) The European Production Efficacy Factor (EEF) was calculated as follows:

$$EEF=[(liveability,\% \times BWgain,kg)/(Study\ duration\ in\ days \times FCR)] \times 100.$$

Statistical Analysis

Statistical unit was 'pen'. Prior to statistical analysis, an outlier test (Grubb's test) was conducted. As a consequence of this procedure no data was excluded from the dataset.

Data of performance was analysed using a bi-factorial ANOVA (procedure PROC GLM) with the fixed effects of lysozyme supplementation as well as their interaction. Differences were investigated between the various levels of each main factor (Tukey test), accounting for multiple comparisons where appropriate.

All statistical analysis was conducted using the software package SAS 9.3.

Results and Discussion

Losses and culls throughout the study ranged from 0.8% to 1.6% over days 8 to 24 for individual treatments. No differences between the treatments were detected.

TABLE 17

FCR and EPEF results using lysozyme (SEQ ID NO: 1)

| Treatment | FCR | FCR change | % improvement | EPEF | EPEF change | % improvement |
|---|---|---|---|---|---|---|
| None | 1.59 | — | — | 315 | — | — |
| Lysozyme | 1.56 | 0.03 | 1.9% | 327 | 12 | 3.8% |

The results show that there was an improvement in both FCR and EPEF when the GH25 lysozyme of SEQ ID NO: 1 was added to the broiler diet compared to when no lysozyme was present.

Example 12: Microbiota Analysis from In Vivo Broiler Trial 4 (Example 11)

The microbiota of broilers from in vivo broiler trial 4 (described in Examples 11) was analysed as described below. 18 chickens from treatment 1 (representing four individual pens) and 30 chickens from treatment 2 (representing four individual pens) were selected for analysis of the microbiota Sampling At the end of the feeding trial chickens selected for microbiota analysis were slaughtered for collection of gut content from the two ceca. The chickens were dissected directly after slaughtering and the intestines were eviscerated. The ceca were then separated from the rest of the intestines by cutting the ceca around 1 cm proximally from the ileocecal junction. This was done by use of a scissor (sterilized in an ethanol bath) or by use of disposable scalpels. The content of the two ceca were emptied collectively into one 15 ml tube. The content of the tube was mixed with an inoculation needle and the digesta was distributed into 4 separate Eppendorf tubes as small aliquots (50-500 mg). The samples were snap-freezed on dry ice and placed in a −80° C. freezer until further processing.

DNA Extraction

DNA was extracted using the "QIAamp Fast DNA Stool Mini Kit" from the company Qiagen. Shortly, each individual sample from the chicken gut (50-250 mg) was suspended in buffer separating inhibitors from DNA. This was followed by bacterial cell lysis. DNA was then adsorbed to a column in the presence of chaotropic salts. Washing steps with high-salt liquid and ethanol were used to remove contaminants and DNA was finally eluted using low-salt or water elution.

PCR Amplification of the 16S RNA Gene

After DNA extraction the extracted DNA was used as template for a PCR reaction targeting the V1-3 variable regions of the 16S rRNA gene.

10-15 ng of extracted DNA was used as template and the PCR reaction (25 μL) contained dNTPs (400 nM of each), MgSO4 (1.5 mM), Platinum® Taq DNA polymerase HF (2 mU), 1× Platinum® High Fidelity buffer (Thermo Fisher Scientific, USA), and barcoded library adaptors (400 nM) containing V3-4 specific primers as follows:

```
Amplification of V1-3 region of 16S RNA gene
Forward primer (27F):
                                        (SEQ ID NO: 10)
AGAGTTTGATCCTGGCTCAG Reverse primer (534R):
                                        (SEQ ID NO: 11)
ATTACCGCGGCTGCTGG
```

PCR settings: Initial denaturation at 95° C. for 2 min, 30 cycles of 95° C. for 20 s, 56° C. for 30 s, 72° C. for 60 s and final elongation at 72° C. for 5 min. The amplicon libraries were purified using the Agencourt® AMpure XP bead protocol (Beckmann Coulter, USA).

DNA Sequencing

The purified sequencing libraries were pooled and samples were paired end sequenced (2×301 bp) on a MiSeq (Illumina) using a MiSeq Reagent kit v3, 600 cycles (Illumina) following the standard guidelines for preparing and loading samples on the MiSeq. 10% Phix control library was spiked in to overcome low complexity issue often observed with amplicon samples.

Bioinformatics Processing, OTU Clustering and Classification

Forward and reverse reads were trimmed for quality using Trimmomatic v. 0.32 (Bolger, Anthony M., Marc Lohse, and Bjoern Usadel. 2014. "Trimmomatic: A flexible trimmer for Illumina sequence data." *Bioinformatics* 30 (15): 2114-20. doi:10.1093/bioinformatics/btu170) with the settings SLIDINGWINDOW:5:3 and MINLEN:275. The trimmed forward and reverse reads were merged using FLASH v. 1.2.7 (Magoc, Tanja, and Steven L Salzberg. 2011. "FLASH: fast length adjustment of short reads to improve genome assemblies." *Bioinformatics* (Oxford, England) 27 (21): 2957-63, doi:10.1093/bioinformatics/btr507) with the settings -m 25-M 200. The merged reads were dereplicated and formatted for use in the UPARSE workflow (Edgar, Robert C. 2013. "UPARSE: highly accurate OTU sequences from microbial amplicon reads." *Nature Methods* 10 (10): 996-8. doi:10.1038/nmeth.2604). The dereplicated reads were clustered, using the usearch v. 7.0.1090-cluster_otus command with default settings. OTU abundances were estimated using the usearch v. 7.0.1090-usearch_global command with -id 0.97. Taxonomy was assigned using the RDP classifier (Wang, Qiong, George M Garrity, James M Tiedje, and James R Cole. 2007. "Naive Bayesian classifierfor rapid assignment of rRNA sequences into the new bacterial taxonomy." *Applied and Environmental Microbiology* 73 (16): 5261-7. doi:10.1128/AEM.00062-07.) as implemented in the parallel_assign_taxonomy_rdp.py script in QIIME (Caporaso, J Gregory, Justin Kuczynski, Jesse Stombaugh, Kyle Bittinger, Frederic D Bushman, Elizabeth K Costello, Noah Fierer, et al. 2010. "QIIME allows analysis of high-throughput community sequencing data." *Nature Methods* 7 (5), Nature Publishing Group: 335-6. doi:10.1038/nmeth.f.303), using the MiDAS database v.1.20 (McIlroy, Simon Jon, Aaron Marc Saunders, Mads Albertsen, Marta Nierychlo, Bianca McIlroy, Aviaja Anna Hansen, Søren Michael Karst, Jeppe Lund Nielsen, and Per Halkjr Nielsen. 2015. "MiDAS: the field guide to the microbes of activated sludge." *Database* 2015 (2): bav062. doi:10.1093/database/bav062).

Statistical Analysis

The results were analysed in R (R Core Team 2015) through the Rstudio IDE using the ampvis package v.1.9.1 (Albertsen, Mads, Søren M Karst, Anja S Ziegler, Rasmus H Kirkegaard, and Per H Nielsen. 2015. "Back to basics—the influence of DNA extraction and primer choice on phylogenetic analysis of activated sludge communities, PLoS ONE 10(7): e0132783, doi:10.1371/journal.pone.0132783), which builds on the R package DESeq2 (Love, Michael I., Wolfgang Huber, and Simon Anders. 2014. "Moderated estimation of fold change and dispersion for RNA-seq data with DESeq2." *Genome Biology* 15 (12): 550. doi:10.1186/s13059-014-0550-8.) for detecting species in differential abundance and vegan (Oksanen, Jari, Guillaume F Blanchet, Roeland Kindt, Pierre Legendre, Peter R. Minchin, R. B. O'Hara, Gavin L. Simpson, Peter Solymos, Henry H. Stevens, and Helene Wagner. 2015. "vegan: Community Ecology Package") for ordination and permutational manova analysis. Pens were used as statistical unit for the statistical analysis of the microbiota, meaning that the abundances of all bacteria were averaged over all the chickens in each individual pen. The detection of species of differential abundance between treatment groups was evaluated by p-values adjusted for multiple testing ($p_{adj}$) such that values of $p_{adj}$ lower than 0.05 were considered significant.

Results

The overall changes in the composition of the chicken gut microbiota upon treatment with SEQ ID NO: 1 are shown in table 18 below.

TABLE 18

Observed shift in the composition of the microbiota compared to the control group

| Trial | Lysozyme | Concentration | Significance[1] | FIG. |
|---|---|---|---|---|
| In vivo trial 4 | SEQ ID NO: 1 | 50 ppm | +++ | FIG. 1 |

[1]Significant change (+++), p-value < 0.05

A significant shift in the microbial composition in the chicken gut is observed upon treatment with the lysozyme of SEQ ID NO: 1 and this effect is coupled to increased European Production Efficiency Factor (EPEF) in chickens.

The observed changes in the composition of the chicken gut microbiota at operational taxonomic unit (OTU) level upon treatment with SEQ ID NO: 1 are shown in table 19.

TABLE 19

Changes in the chicken gut microbiota at OTU level from in vivo broiler trial 4

| OTU level | p-value | $p_{adj}$ | Control[1] | Lysozyme[2] | Change | Ratio | Tax. Assignment[3] (genus level) |
|---|---|---|---|---|---|---|---|
| OTU #27 | 0.0010 | 0.0145 | 0.22 | 3.67 | 3.45 | 16.53 | *Faecalibacterium* |

[1]Treatment 1 (no lysozyme);
[2]Treatment 2 (Lysozyme, SEQ ID NO: 1)
[3]Taxonomy Assignment Treatment with SEQ ID NO: 1 leads to a higher proportion of a bacterial species of the genus *Faecalibacterium* in the chicken gut and this shift is associated with increased European Production Efficiency Factor (EPEF) in chickens and this bacterial species has 96% identity to the species *Faecalibacterium prausnitzii*.

The observed changes in the composition of the chicken gut microbiota at genus level upon treatment with SEQ ID NO: 1 are shown in table 20 below.

TABLE 20

Changes in the chicken gut microbiota at genus level from in vivo broiler trial 4

| Genus level | p-value | $p_{adj}$ | Control[1] | Lysozyme[2] | Change | Ratio |
|---|---|---|---|---|---|---|
| *Faecalibacterium* | 0.123 | 0.282 | 1.86 | 7.50 | 5.65 | 4.04 |

[1]Treatment 1 (no lysozyme);
[2]Treatment 2 (Lysozyme, SEQ ID NO: 1)

Treatment with SEQ ID NO: 1 leads to a higher proportion of bacteria of the genus *Faecalibacterium* in the chicken gut and this shift is associated with increased European Production Efficiency Factor (EPEF) in chickens.

The observed changes in the composition of the chicken gut microbiota at order level upon treatment with SEQ ID NO: 1 are shown in table 21 below.

TABLE 21

Changes in the chicken gut microbiota at order level from in vivo broiler trial 4

| Order level | p-value | $p_{adj}$ | Control[1] | Lysozyme[2] | Change | Ratio |
|---|---|---|---|---|---|---|
| Clostridiales | 0.0071 | 0.0570 | 32.1846 | 37.5638 | 5.3792 | 1.1671 |
| Bacteroidales | 0.0779 | 0.2078 | 64.3989 | 48.5437 | −15.8551 | 0.7538 |

[1]Treatment 1 (no lysozyme);
[2]Treatment 2 (Lysozyme, SEQ ID NO: 1)

Treatment with SEQ ID NO: 1 leads to a higher proportion of bacteria of the order Clostridiales in the chicken gut and this shift is associated with increased European Production Efficiency Factor (EPEF) in chickens.

Treatment with SEQ ID NO: 1 leads to a lower proportion of bacteria of the order Bacteroidales in the chicken gut and this shift is associated with increased European Production Efficiency Factor (EPEF) in chickens.

A summary of the observed shift in the composition of the microbiota compared to the control group is presented in table 22 below.

TABLE 22

Observed shift in the composition of the microbiota compared to the control group

| | Significance[1] | FIG. |
|---|---|---|
| OTU level (*Faecalibacierium* species) | | |
| In vivo trial 4 (SEQ ID NO: 1 at 50 ppm) Genus level (*Faecalibacterium*) | +++ | FIG. 2 |
| In vivo trial 4 (SEQ ID NO: 1 at 50 ppm) Order level (Clostridiales) | + | FIG. 3 |
| In vivo trial 4 (SEQ ID NO: 1 at 50 ppm) Order level (Bacteroidales) | + | FIG. 4 |
| In vivo trial 4 (SEQ ID NO: 1 at 50 ppm) | + | FIG. 4 |

[1]Significant change (+++), $p_{adj}$ < 0.05, Numerical change (+)

In conclusion it can be seen that the GH25 lysozymes induced a significant shift in the microbial composition in the chicken gut and this effect is coupled to an increased European Production Efficiency Factor (EPEF) in chickens. Treatment with the GH25 lysozyme led to a higher proportion of bacterial species within the genus *Faecalibacterium*, and overall increased the proportion of bacteria of the order Clostridiales and decreased bacteria of the order Bacteroidales.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method of improving the European Production Efficiency Factor (EPEF) and/or feed conversion ratio (FCR) of a monogastric animal comprising administering an animal feed or animal feed additive comprising one or more microbial lysozymes to the monogastric animal wherein the microbial lysozyme is administered at a level of 8 to 250 ppm enzyme protein per kg animal feed and the microbial lysozyme
   (a) has at least 95% sequence identity to SEQ ID NO: 1, 4 or 12, or
   (b) is a fragment of SEQ ID NO: 1 comprising at least 200 amino acids; a fragment of SEQ ID NO: 4 comprising at least 240 amino acids; or a fragment of SEQ ID NO: 12 comprising at least 200 amino acids.

2. The method of claim 1, wherein the FCR is improved by at least 1.0% compared to control.

3. The method of claim 1, wherein the EPEF is improved by at least 1.0% compared to control.

4. The method of claim 1, wherein the microbial lysozyme has antimicrobial activity toward *Clostridium perfringens*.

5. The method of claim 1, wherein the animal feed or animal feed additive increases the proportion of bacteria of genus *Faecalibacterium* in the microbiota of the GI tract of an animal.

6. The method of claim 5, wherein the proportion of bacteria of genus *Faecalibacterium* is increased by at least 1%.

7. The method of claim 5, wherein the proportion of bacteria of genus *Faecalibacterium* is increased by a factor of at least 1.25.

8. The method of claim 1, wherein the animal feed or animal feed additive improves the European Production Efficiency Factor (EPEF) and/or Feed Conversion Ratio (FCR) of an animal by at least 1% compared to control and increases the proportion of bacteria of genus *Faecalibacterium* in the microbiota of the GI tract of an animal.

9. The method of claim 8, wherein the proportion of bacteria of genus *Faecalibacterium* is increased by at least 1%.

10. The method of claim 8, wherein the proportion of bacteria of genus *Faecalibacterium* is increased by a factor of at least 1.25.

11. The method of claim 1, wherein the monogastric animal is selected from the group consisting of swine, piglet, growing pig, sow, poultry, turkey, duck, quail, guinea fowl, goose, pigeon, squab, chicken, broiler, layer, pullet and chick, horse, crustaceans, shrimps, prawns, fish, amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish.

12. The method of claim 1, wherein the monogastric animal is selected from the group consisting of swine, piglet, growing pig, sow, chicken, broiler, layer, pullet and chick.

13. The method of claim 1, wherein the microbial lysozyme is fed to the animal during the life span of the animal.

14. The method of claim 1, wherein the microbial lysozyme is fed to broilers during the pre-starter (days 1-7) and/or starter (days 8-22) period or to piglets during the pre-starter (days 1-14 after weaning) and/or starter (days 15-42 after weaning) period.

15. The method of claim 1, wherein the microbial lysozyme is obtained or obtainable from the phylum Ascomycota.

16. The method of claim 1, wherein the microbial lysozyme is obtained or obtainable from the subphylum Pezizomycotina.

17. The method of claim 1, wherein the microbial lysozyme comprises one or more domains selected from the list consisting of GH24 and GH25.

18. The method of claim 1, wherein the microbial lysozyme is selected from the group consisting of amino acids 1 to 213 of SEQ ID NO: 1, amino acids 1 to 245 of SEQ ID NO: 4 and amino acids 1 to 208 of SEQ ID NO: 12.

* * * * *

```
                          SEQUENCE LISTING

<160> NUMBER OF SEQ ID NOS: 15

<210> SEQ ID NO 1
<211> LENGTH: 213
<212> TYPE: PRT
<213> ORGANISM: Artificial Sequence
<220> FEATURE:
<223> OTHER INFORMATION: Wild type sequence with N-terminal SPIRR

<400> SEQUENCE: 1

Ser Pro Ile Arg Arg Ile Pro Gly Phe Asp Ile Ser Gly Trp Gln
 1               5                  10                  15

Pro Thr Thr Asp Phe Ala Arg Ala Tyr Ala Asn Gly Asp Arg Phe Val
                 20                  25                  30

Tyr Ile Lys Ala Thr Glu Gly Thr Thr Phe Lys Ser Ser Ala Phe Ser
                 35                  40                  45

Arg Gln Tyr Thr Gly Ala Thr Gln Asn Gly Phe Ile Arg Gly Ala Tyr
         50                  55                  60

His Phe Ala Gln Pro Ala Ala Ser Ser Gly Ala Ala Gln Ala Arg Tyr
 65                  70                  75                  80

Phe Ala Ser Asn Gly Gly Gly Trp Ser Lys Asp Gly Ile Thr Leu Pro
                 85                  90                  95

Gly Ala Leu Asp Ile Glu Tyr Asn Pro Asn Gly Ala Thr Cys Tyr Gly
                100                 105                 110

Leu Ser Gln Ser Ala Met Val Asn Trp Ile Glu Asp Phe Val Thr Thr
                115                 120                 125

Tyr His Gly Ile Thr Ser Arg Trp Pro Val Ile Tyr Thr Thr Thr Asp
        130                 135                 140

Trp Trp Thr Gln Cys Thr Gly Asn Ser Asn Arg Phe Ala Asn Arg Cys
145                 150                 155                 160

Pro Leu Trp Ile Ala Arg Tyr Ala Ser Ser Val Gly Thr Leu Pro Asn
                165                 170                 175

Gly Trp Gly Phe Tyr Thr Phe Trp Gln Tyr Asn Asp Lys Tyr Pro Gln
                180                 185                 190

Gly Gly Asp Ser Asn Trp Phe Asn Gly Asp Ala Ser Arg Leu Arg Ala
                195                 200                 205

Leu Ala Asn Gly Asp
        210

<210> SEQ ID NO 2
<211> LENGTH: 946
<212> TYPE: DNA
<213> ORGANISM: Trichophaea saccata
<220> FEATURE:
<221> NAME/KEY: CDS
<222> LOCATION: (1)..(347)
<220> FEATURE:
<221> NAME/KEY: sig_peptide
<222> LOCATION: (1)..(51)
<220> FEATURE:
<221> NAME/KEY: mat_peptide
<222> LOCATION: (52)..(943)
<220> FEATURE:
<221> NAME/KEY: CDS
<222> LOCATION: (401)..(615)
```

```
<220> FEATURE:
<221> NAME/KEY: CDS
<222> LOCATION: (668)..(772)
<220> FEATURE:
<221> NAME/KEY: CDS
<222> LOCATION: (825)..(943)

<400> SEQUENCE: 2 atg cac gct ctc acc ctt ctc acc gca acc ctc ttc ggt ctc gca gcg      48
Met His Ala Leu Thr Leu Leu Thr Ala Thr Leu Phe Gly Leu Ala Ala
        -15                 -10                 -5 gcc tac cca gtg aag acc gac ctt cac tgc cgc tcc tct ccc agc act      96
Ala Tyr Pro Val Lys Thr Asp Leu His Cys Arg Ser Ser Pro Ser Thr
 -1  1               5                  10                  15 tcc gcc agc atc gtc cgc acc tac tcc agt gga acg gaa gtc cag atc     144
Ser Ala Ser Ile Val Arg Thr Tyr Ser Ser Gly Thr Glu Val Gln Ile
                20                  25                  30 cag tgc cag acc acg ggc act tcg gtc caa gga tcc aat gtc tgg gac     192
Gln Cys Gln Thr Thr Gly Thr Ser Val Gln Gly Ser Asn Val Trp Asp
            35                  40                  45 aag acc cag cac ggt tgc tac gtc gca gac tac tac gtc aag acc ggg     240
Lys Thr Gln His Gly Cys Tyr Val Ala Asp Tyr Tyr Val Lys Thr Gly
        50                  55                  60 cat tct ggg att ttc acc acc aag tgc ggt agc agc tcg ggt gga ggt     288
His Ser Gly Ile Phe Thr Thr Lys Cys Gly Ser Ser Ser Gly Gly Gly
 65                  70                  75 tcc tgc aag cct ccc ccg atc aat gct gct act gtc gca ttg atc aag     336
Ser Cys Lys Pro Pro Pro Ile Asn Ala Ala Thr Val Ala Leu Ile Lys
 80                  85                  90                  95 gag ttt gag gg  gtaagtgaca gctctgagtg aggtggtatg aggattaaga         387
Glu Phe Glu Gly ctgacgagga tag a ttc gtt cct aag ccc gcc ccg gat cct att gga ttg    437
                 Phe Val Pro Lys Pro Ala Pro Asp Pro Ile Gly Leu
                 100                 105                 110 ccg acc gtg gga tac ggg cat ctt tgc aag act aag ggc tgc aaa gaa     485
Pro Thr Val Gly Tyr Gly His Leu Cys Lys Thr Lys Gly Cys Lys Glu
            115                 120                 125 gtg cct tac agc ttc cct ctc acc cag gag act gcc acc aag ttg ctt     533
Val Pro Tyr Ser Phe Pro Leu Thr Gln Glu Thr Ala Thr Lys Leu Leu
        130                 135                 140 cag agc gat atc aag act ttc acc tct tgc gtt agc aac tac gtc aag     581
Gln Ser Asp Ile Lys Thr Phe Thr Ser Cys Val Ser Asn Tyr Val Lys
    145                 150                 155 gac tct gtt aag ctc aac gat aac cag tac gga g gtgagttcca            625
Asp Ser Val Lys Leu Asn Asp Asn Gln Tyr Gly
160                 165                 170 gtgtaacagt gaatttattg atgatattct aagtaatttt ag ct  ctg gcg tct      678
                                                  Ala Leu Ala Ser tgg gct ttc aac gtc ggc tgc gga aac gtc cag act tct tcg ctg atc     726
Trp Ala Phe Asn Val Gly Cys Gly Asn Val Gln Thr Ser Ser Leu Ile
175                 180                 185                 190 aag aga ttg aac gct ggg gag aac cct aac act gtc gct gct cag g       772
Lys Arg Leu Asn Ala Gly Glu Asn Pro Asn Thr Val Ala Ala Gln
                195                 200                 205 gtaagatatt tatcccggat ttgctcttga cacatggctg aaaaagttgc ag aa ctc    829
                                                          Glu Leu ccc aag tgg aag tac gct ggt gga aag gtt atg cct ggc ttg gtc cgc     877
Pro Lys Trp Lys Tyr Ala Gly Gly Lys Val Met Pro Gly Leu Val Arg
        210                 215                 220 cgc cgc aat gct gag gtc gcg ctc ttc aag aag ccc agc agc gtt cag     925
Arg Arg Asn Ala Glu Val Ala Leu Phe Lys Lys Pro Ser Ser Val Gln
```

```
Arg Arg Asn Ala Glu Val Ala Leu Phe Lys Lys Pro Ser Ser Val Gln
    225                 230                 235 gcc cac cct ccc aag tgc taa                                          946
Ala His Pro Pro Lys Cys
240                 245

<210> SEQ ID NO 3
<211> LENGTH: 262
<212> TYPE: PRT
<213> ORGANISM: Trichophaea saccata

<400> SEQUENCE: 3

Met His Ala Leu Thr Leu Leu Thr Ala Thr Leu Phe Gly Leu Ala Ala
        -15                 -10                  -5

Ala Tyr Pro Val Lys Thr Asp Leu His Cys Arg Ser Ser Pro Ser Thr
 -1  1               5                  10                  15

Ser Ala Ser Ile Val Arg Thr Tyr Ser Ser Gly Thr Glu Val Gln Ile
                20                  25                  30

Gln Cys Gln Thr Thr Gly Thr Ser Val Gln Gly Ser Asn Val Trp Asp
             35                  40                  45

Lys Thr Gln His Gly Cys Tyr Val Ala Asp Tyr Tyr Val Lys Thr Gly
         50                  55                  60

His Ser Gly Ile Phe Thr Thr Lys Cys Gly Ser Ser Gly Gly Gly
 65                  70                  75

Ser Cys Lys Pro Pro Ile Asn Ala Ala Thr Val Ala Leu Ile Lys
80                  85                  90                  95

Glu Phe Glu Gly Phe Val Pro Lys Pro Ala Pro Asp Pro Ile Gly Leu
                100                 105                 110

Pro Thr Val Gly Tyr Gly His Leu Cys Lys Thr Lys Gly Cys Lys Glu
            115                 120                 125

Val Pro Tyr Ser Phe Pro Leu Thr Gln Glu Thr Ala Thr Lys Leu Leu
        130                 135                 140

Gln Ser Asp Ile Lys Thr Phe Thr Ser Cys Val Ser Asn Tyr Val Lys
    145                 150                 155

Asp Ser Val Lys Leu Asn Asp Asn Gln Tyr Gly Ala Leu Ala Ser Trp
160                 165                 170                 175

Ala Phe Asn Val Gly Cys Gly Asn Val Gln Thr Ser Ser Leu Ile Lys
                180                 185                 190

Arg Leu Asn Ala Gly Glu Asn Pro Asn Thr Val Ala Ala Gln Glu Leu
            195                 200                 205

Pro Lys Trp Lys Tyr Ala Gly Gly Lys Val Met Pro Gly Leu Val Arg
        210                 215                 220

Arg Arg Asn Ala Glu Val Ala Leu Phe Lys Lys Pro Ser Ser Val Gln
    225                 230                 235

Ala His Pro Pro Lys Cys
240                 245

<210> SEQ ID NO 4
<211> LENGTH: 245
<212> TYPE: PRT
<213> ORGANISM: Trichophaea saccata
<220> FEATURE:
<221> NAME/KEY: mat_peptide
<222> LOCATION: (1)..(245)

<400> SEQUENCE: 4

Tyr Pro Val Lys Thr Asp Leu His Cys Arg Ser Ser Pro Ser Thr Ser
 1               5                  10                  15
```

```
Ala Ser Ile Val Arg Thr Tyr Ser Ser Gly Thr Glu Val Gln Ile Gln
         20                  25                  30

Cys Gln Thr Thr Gly Thr Ser Val Gln Gly Ser Asn Val Trp Asp Lys
             35                  40                  45

Thr Gln His Gly Cys Tyr Val Ala Asp Tyr Val Lys Thr Gly His
     50                  55                  60

Ser Gly Ile Phe Thr Thr Lys Cys Gly Ser Ser Gly Gly Ser
 65              70                  75                  80

Cys Lys Pro Pro Ile Asn Ala Ala Thr Val Ala Leu Ile Lys Glu
                 85                  90                  95

Phe Glu Gly Phe Val Pro Lys Pro Ala Pro Asp Pro Ile Gly Leu Pro
             100                 105                 110

Thr Val Gly Tyr Gly His Leu Cys Lys Thr Lys Gly Cys Lys Glu Val
             115                 120                 125

Pro Tyr Ser Phe Pro Leu Thr Gln Glu Thr Ala Thr Lys Leu Leu Gln
 130                 135                 140

Ser Asp Ile Lys Thr Phe Thr Ser Cys Val Ser Asn Tyr Val Lys Asp
 145                 150                 155                 160

Ser Val Lys Leu Asn Asp Asn Gln Tyr Gly Ala Leu Ala Ser Trp Ala
                 165                 170                 175

Phe Asn Val Gly Cys Gly Asn Val Gln Thr Ser Ser Leu Ile Lys Arg
             180                 185                 190

Leu Asn Ala Gly Glu Asn Pro Asn Thr Val Ala Gln Glu Leu Pro
     195                 200                 205

Lys Trp Lys Tyr Ala Gly Gly Lys Val Met Pro Gly Leu Val Arg Arg
 210                 215                 220

Arg Asn Ala Glu Val Ala Leu Phe Lys Lys Pro Ser Ser Val Gln Ala
225                 230                 235                 240

His Pro Pro Lys Cys
                245

<210> SEQ ID NO 5
<211> LENGTH: 129
<212> TYPE: PRT
<213> ORGANISM: Gallus gallus

<400> SEQUENCE: 5

Lys Val Phe Gly Arg Cys Glu Leu Ala Ala Ala Met Lys Arg His Gly
1                5                  10                  15

Leu Asp Asn Tyr Arg Gly Tyr Ser Leu Gly Asn Trp Val Cys Ala Ala
             20                  25                  30

Lys Phe Glu Ser Asn Phe Asn Thr Gln Ala Thr Asn Arg Asn Thr Asp
         35                  40                  45

Gly Ser Thr Asp Tyr Gly Ile Leu Gln Ile Asn Ser Arg Trp Trp Cys
     50                  55                  60

Asn Asp Gly Arg Thr Pro Gly Ser Arg Asn Leu Cys Asn Ile Pro Cys
 65              70                  75                  80

Ser Ala Leu Leu Ser Ser Asp Ile Thr Ala Ser Val Asn Cys Ala Lys
                 85                  90                  95

Lys Ile Val Ser Asp Gly Asn Gly Met Asn Ala Trp Val Ala Trp Arg
             100                 105                 110

Asn Arg Cys Lys Gly Thr Asp Val Gln Ala Trp Ile Arg Gly Cys Arg
         115                 120                 125

Leu
```

```
<210> SEQ ID NO 6
<211> LENGTH: 39
<212> TYPE: DNA
<213> ORGANISM: Artificial Sequence
<220> FEATURE:
<223> OTHER INFORMATION: Primer F-80470

<400> SEQUENCE: 6
acacaactgg ggatccacca tgcacgctct cacccttct                              39

<210> SEQ ID NO 7
<211> LENGTH: 38
<212> TYPE: DNA
<213> ORGANISM: Artificial Sequence
<220> FEATURE:
<223> OTHER INFORMATION: Primer R-80470.

<400> SEQUENCE: 7
ctagatctcg agaagctttt agcacttggg agggtggg                               38

<210> SEQ ID NO 8
<211> LENGTH: 20
<212> TYPE: DNA
<213> ORGANISM: Artificial Sequence
<220> FEATURE:
<223> OTHER INFORMATION: Primer 8643.

<400> SEQUENCE: 8
gcaagggatg ccatgcttgg                                                   20

<210> SEQ ID NO 9
<211> LENGTH: 19
<212> TYPE: DNA
<213> ORGANISM: Artificial Sequence
<220> FEATURE:
<223> OTHER INFORMATION: Primer 8654.

<400> SEQUENCE: 9
catataacca attgccctc                                                    19

<210> SEQ ID NO 10
<211> LENGTH: 20
<212> TYPE: DNA
<213> ORGANISM: Artificial Sequence
<220> FEATURE:
<223> OTHER INFORMATION: Forward primer 27F.

<400> SEQUENCE: 10
agagtttgat cctggctcag                                                   20

<210> SEQ ID NO 11
<211> LENGTH: 17
<212> TYPE: DNA
<213> ORGANISM: Artificial Sequence
<220> FEATURE:
<223> OTHER INFORMATION: Reverse primer 534R.

<400> SEQUENCE: 11
attaccgcgg ctgctgg                                                      17

<210> SEQ ID NO 12
<211> LENGTH: 213
<212> TYPE: PRT
<213> ORGANISM: Acremonium alcalophilum
```

<400> SEQUENCE: 12

| | | | | | | | | | | | | | | |
|---|---|---|---|---|---|---|---|---|---|---|---|---|---|---|
|Ser|Pro|Ile|Arg|Arg|Ile|Pro|Gly|Phe|Asp|Ile|Ser|Gly|Trp|Gln|
|1| | |  |5| | | | |10| | | | |15|
|Pro|Thr|Thr|Asp|Phe|Ala|Arg|Ala|Tyr|Ala|Asn|Gly|Asp|Arg|Phe|Val|
| | | |20| | | | |25| | | | |30| |
|Tyr|Ile|Lys|Ala|Thr|Glu|Gly|Thr|Phe|Lys|Ser|Ser|Ala|Phe|Ser|
| | |35| | | | |40| | | | |45| | |
|Arg|Gln|Tyr|Thr|Gly|Ala|Thr|Gln|Asn|Gly|Phe|Ile|Arg|Gly|Ala|Tyr|
| |50| | | | |55| | | | |60| | | |
|His|Phe|Ala|Gln|Pro|Ala|Ala|Ser|Ser|Gly|Ala|Ala|Gln|Ala|Arg|Tyr|
|65| | | |70| | | |75| | | | |80| |
|Phe|Ala|Ser|Asn|Gly|Gly|Trp|Ser|Lys|Asp|Gly|Ile|Thr|Leu|Pro|
| | | | |85| | | |90| | | | |95| |
|Gly|Ala|Leu|Asp|Ile|Glu|Tyr|Asn|Pro|Asn|Gly|Ala|Thr|Cys|Tyr|Gly|
| | | |100| | | |105| | | | |110| | |
|Leu|Ser|Gln|Ser|Ala|Met|Val|Asn|Trp|Ile|Glu|Asp|Phe|Val|Thr|Thr|
| | |115| | | |120| | | | |125| | | |
|Tyr|His|Gly|Ile|Thr|Ser|Arg|Trp|Pro|Val|Ile|Tyr|Thr|Thr|Thr|Asp|
| |130| | | |135| | | | |140| | | | |
|Trp|Trp|Thr|Gln|Cys|Thr|Gly|Asn|Ser|Asn|Arg|Phe|Ala|Asn|Arg|Cys|
|145| | | |150| | | |155| | | | |160| |
|Pro|Leu|Trp|Ile|Ala|Arg|Tyr|Ala|Ser|Ser|Val|Gly|Thr|Leu|Pro|Asn|
| | | |165| | | |170| | | | |175| | |
|Gly|Trp|Gly|Phe|Tyr|Thr|Phe|Trp|Gln|Tyr|Asn|Asp|Lys|Tyr|Pro|Gln|
| | |180| | | |185| | | | |190| | | |
|Gly|Gly|Asp|Ser|Asn|Trp|Phe|Asn|Gly|Asp|Ala|Ser|Arg|Leu|Arg|Ala|
| |195| | | |200| | | | |205| | | | |
|Leu|Ala|Asn|Gly|Asp|
| |210| | | | |

<210> SEQ ID NO 13
<211> LENGTH: 470
<212> TYPE: DNA
<213> ORGANISM: Faecalibacterium sp.

<400> SEQUENCE: 13

```
gacgaacgct ggcggcgcgc ctaacacatg caagtcgaac ggaatgcgga gaggatttat      60
cttttctgtg tttagtggcg aacgggtgag taacgcgtga ggaacctgcc tcaaagaggg     120
ggacaacagt tggaaacgac tgctaatacc gcataagccc acggggccgc atggctctga     180
gggaaaagga gcaatccgct ttgagatggc ctcgcgtccg attagctggt tggtgaggta     240
acggcccacc aaggcgacga tcggtagccg gactgagagg ttgaacggcc acattgggac     300
tgagacacgg cccagactcc tacgggaggc agcagtgggg aatattgcac aatgggggaa     360
accctgatgc agcgacgccg cgtggaggaa gaaggtcttc ggattgtaaa ctcctgttgt     420
tgggaaaag aaggatggta cccaacaagg aagtgacggc taactacgtg               470
```

<210> SEQ ID NO 14
<211> LENGTH: 468
<212> TYPE: DNA
<213> ORGANISM: Faecalibacterium sp.

<400> SEQUENCE: 14

```
gacgaacgct ggcggcgcgc ctaacacatg caagtcgaac ggagttgaga ggagcttgct      60
tttcttgact tagtggcgaa cgggtgagta acgcgtgagg aacctgcctc aaagaggggg     120
```

-continued

```
acaacagttg gaaacgactg ctaataccgc ataagcccac ggtcccgcat gggagagagg      180
gaaaaggagc aatccgcttt gagatggcct cgcgtccgat tagctagttg gtgaggtaac      240
ggcccaccaa ggcgacgatc ggtagccgga ctgagaggtt gaacggccac attgggactg      300
agacacggcc cagactccta cgggaggcag cagtggggaa tattgcacaa tggggggaaac    360 cctgatgcag cgacgccgcg tggaggaaga aggtcttcgg attgtaaact cctgttgttg     420
gggaaaaaga ggatggtacc caacaaggaa gtgacggcta actacgtg                  468
```

<210> SEQ ID NO 15
<211> LENGTH: 468
<212> TYPE: DNA
<213> ORGANISM: Faecalibacterium sp.

<400> SEQUENCE: 15

```
gacgaacgct ggcggcgcgc ctaacacatg caagtcgaac ggagcttgag ggagcttgct      60
tctttaagct tagtggcgaa cgggtgagta acgcgtgagg aacctgcctc agagtggggg     120
acaacagttg gaaacgactg ctaataccgc ataagcccac ggatccgcat ggatctgagg     180
gaaaaggagc aatccgcttt gagatggcct cgcgtccgat tagctggttg gtgaggtaac     240
ggcccaccaa ggcgacgatc ggtagccgga ctgagaggtt gaacggccac attgggactg     300
agacacggcc cagactccta cgggaggcag cagtggggaa tattgcacaa tggggggaaac    360 cctgatgcag cgacgccgcg tggaggaaga aggtcttcgg attgtaaact cctgttgtta    420
gggaaaatcg agatggtacc taacaaggaa gtgacggcta actacgtg                  468
```